(12) United States Patent
Temple et al.

(10) Patent No.: US 9,047,397 B1
(45) Date of Patent: Jun. 2, 2015

(54) RADIOGRAPH AND PASSIVE DATA ANALYSIS USING MIXED VARIABLE OPTIMIZATION

(71) Applicant: Los Alamos National Security, LLC, Los Alamos, NM (US)

(72) Inventors: Brian A. Temple, Los Alamos, NM (US); Jerawan C. Armstrong, Los Alamos, NM (US); Kevin L. Buescher, White Rock, NM (US); Jeffrey A. Favorite, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 272 days.

(21) Appl. No.: 13/631,607

(22) Filed: Sep. 28, 2012

Related U.S. Application Data

(60) Provisional application No. 61/640,716, filed on Apr. 30, 2012, provisional application No. 61/663,472, filed on Jun. 22, 2012.

(51) Int. Cl.
*G06K 9/00* (2006.01)
*G06F 19/00* (2011.01)

(52) U.S. Cl.
CPC .................................. *G06F 19/345* (2013.01)

(58) Field of Classification Search
CPC ......... G01T 1/167; G01T 7/00; G01T 1/1642; G01T 1/1644; G01T 1/1647; G01T 1/2985; B29C 33/38; G01N 2223/423; G01N 23/22; G01N 25/72; G01V 5/0008; G06K 9/00

USPC .................................................. 382/131, 132
See application file for complete search history.

(56) References Cited

U.S. PATENT DOCUMENTS

| | | | | |
|---|---|---|---|---|
| 5,168,161 A | * | 12/1992 | Markandey | 250/330 |
| 5,373,538 A | * | 12/1994 | Grenier et al. | 376/159 |
| 5,479,023 A | * | 12/1995 | Bartle | 250/390.04 |
| 5,600,303 A | * | 2/1997 | Husseiny et al. | 340/568.1 |
| 6,484,051 B1 | * | 11/2002 | Daniel | 600/436 |
| 7,161,150 B2 | * | 1/2007 | Frankle et al. | 250/339.06 |
| 7,897,932 B2 | * | 3/2011 | DeVito | 250/370.11 |

OTHER PUBLICATIONS

Abramson et al., "Quantitative Object Reconstruction Using Abel Transform X-Ray Tomography and Mixed Variable Optimization," *SIAM J. Imaging Sciences*, vol. 1, No. 3, pp. 322-342 (Sep. 2008).

(Continued)

*Primary Examiner* — Tom Y Lu
(74) *Attorney, Agent, or Firm* — Klarquist Sparkman, LLP

(57) ABSTRACT

Disclosed herein are representative embodiments of methods, apparatus, and systems for performing radiography analysis. For example, certain embodiments perform radiographic analysis using mixed variable computation techniques. One exemplary system comprises a radiation source, a two-dimensional detector for detecting radiation transmitted through a object between the radiation source and detector, and a computer. In this embodiment, the computer is configured to input the radiographic image data from the two-dimensional detector and to determine one or more materials that form the object by using an iterative analysis technique that selects the one or more materials from hierarchically arranged solution spaces of discrete material possibilities and selects the layer interfaces from the optimization of the continuous interface data.

30 Claims, 16 Drawing Sheets

(56) References Cited

OTHER PUBLICATIONS

Armstrong et al., "Identification of Unknown Interface Locations in a Source/Shield System Using the Mesh Adaptive Direct Search Method," *American Nuclear Society Annual Meeting*, LA-UR-12-22365, 14 pp. (Jun. 2012).

Asaki, "Quantitative Abel tomography robust to noisy, corrupted and missing data," *Optim Eng.*, vol. 11, pp. 381-393 (Sep. 2010).

Le Digabel, "Algorithm 909: NOMAD: Nonlinear Optimization with the MADS Algorithm," *ACM Trans. on Mathematical Software*, vol. 37, Issue 4, 15 pp. (Feb. 2011).

O'Reilly, "Quantitative Object Reconstruction using Abel Transform Tomography and Mixed Variable Optimization," Thesis, Air Force Institute of Technology, 97 pp. (document dated Mar. 2006).

* cited by examiner

RADIOGRAPH AND PASSIVE DATA ANALYSIS USING MIXED VARIABLE OPTIMIZATION

CROSS-REFERENCE TO RELATED APPLICATIONS

This application claims the benefit of U.S. Provisional Application No. 61/640,716, filed on Apr. 30, 2012, and entitled "RADIOGRAPHY ANALYSIS USING MIXED VARIABLE OPTIMIZATION" and the benefit of U.S. Provisional Application No. 61/663,472, filed on Jun. 22, 2012, and entitled "RADIOGRAPHY ANALYSIS USING MIXED VARIABLE OPTIMIZATION", both of which are hereby incorporated herein in their entirety.

ACKNOWLEDGEMENT OF GOVERNMENT SUPPORT

This invention was made with government support under Contract No. DEAC52-06NA25396 awarded by the U.S. Department of Energy. The government has certain rights in the invention.

FIELD

This application relates to the field of radiography analysis and passive data analysis.

SUMMARY

Disclosed below are representative embodiments of methods, apparatus, and systems for performing radiography analysis. For example, certain embodiments perform radiographic analysis using mixed variable computation techniques. The disclosed methods, apparatus, and systems should not be construed as limiting in any way. Instead, the present disclosure is directed toward all novel and/or nonobvious features and aspects of the various disclosed embodiments, alone or in various combinations and subcombinations with one another.

The example embodiments disclosed herein include a radiographic analysis method comprising: receiving radiographic image data of a spherically or cylindrically symmetric object; performing a linear inversion of data derived from the radiographic image data; establishing an initial estimate for interface locations between one or more layers of the object; determining the interface locations for one or more of the layers of the object and identifications of one or more materials forming one or more of the layers of the object, wherein the interface locations are treated as continuous variables and the identifications of the one or more materials are treated as discrete variables during the determining; and outputting the one or more interface locations and the identifications of the one or more materials forming the one or more of the layers of the object. The method can further comprise displaying the linear inversion of the radiographic image data, and wherein the establishing the initial estimate comprises receiving input from a user concerning the interface locations of one or more layers of the object. In certain implementations, the linear inversion is an Abel inversion. In certain implementations, the method also comprises establishing a center of the object from which one or more radial line plots determined from averaging regions of the image. For example, the radiographic image data can be displayed, and the center of the object can be established by receiving input from a user concerning the center. In particular implementations, the unknown object data is obtained passively without any external radiation source, while in other implementations, radiographic image data is obtained using an external radiation source that interrogates the object. In particular implementations, the unknown object data can be obtained both passively and from the interrogation of the object from an external source. The disclosed methods can be implemented as software stored on a computer-readable medium. For example, embodiments of the disclosed method can comprise one or more non-transitory computer-readable media storing computer-executable instructions which when executed by a computer cause the computer to perform the method.

The example embodiments disclosed herein also include a radiographic analysis method comprising: receiving radiographic image data of an unknown spherically or cylindrically symmetric object; and determining one or more materials forming one or more layers of the spherically or cylindrically symmetric object. In particular implementations, the determining is based at least in part on the radiographic image data and comprises: during a first iteration, selecting a first material from a first solution space of discrete variables consisting of a first subset of less than all possible materials, and, during a second iteration, selecting a second material from a second solution space of discrete variables consisting of a second subset of less than all possible materials, the second subset being different from the first subset. The second solution space can comprise materials that are nearer in density to one another than the materials in the first second solution. Further, the second solution space can comprise one or two materials that are nearest neighbors to the material selected in the first iteration, and the first solution space can be constrained to exclude materials that are nearest neighbors to the material selected. In certain implementations, the first solution space and the second solution space are part of a hierarchically arranged set of discrete variable solution spaces. In some implementations, the method additionally comprises selecting an interface location for one or more object layers from a solution space of continuous variables. In certain implementations, the method further comprises obtaining initial estimates of an interface location for one or more object layers, a material for one or more of the object layers, or both an interface location and a material for one or more of the object layers. In some implementations, the method further comprises performing an Abel inversion on a radial line plot derived from the radiographic image data. In certain implementations, the radiographic image is created from data generated by a detector detecting radiation transmitted through the unknown object that originates from a radiation source separate from the unknown spherically or cylindrically symmetric object. In other implementations, data from the object is obtained passively without a radiation source separate from the unknown spherically or cylindrically symmetric object. The disclosed methods can be implemented as software stored on a computer-readable medium. For example, embodiments of the disclosed method can comprise one or more non-transitory computer-readable media storing computer-executable instructions which when executed by a computer cause the computer to perform the method.

The example embodiments disclosed herein also include a system comprising: a radiation source; a two-dimensional detector for detecting radiation transmitted through the spherically or cylindrically symmetric object originating from the radiation source; and a computer configured to input the radiographic image data from the two-dimensional detector and use an iterative analysis technique that selects the one or more materials from hierarchically arranged solution spaces of discrete material possibilities. In certain implementations, the analysis technique also selects the layer interfaces from an optimization of continuous interface data. In certain implementations, a first iteration of the iterative analysis technique uses a higher-order solution space than a solution space for a second iteration, and the solution space for the second iteration includes additional discrete material possibilities not present in the higher-order solution space for the first iteration. The additional discrete material possibilities in the second solution space can comprise materials that are closer in density to one another than the discrete material possibilities in the first solution space. In some implementations, the computer is further configured to perform a linear inversion of a radial line plot derived from the radiographic image data. In certain implementations, the computer is further configured to compute a scatter field based at least in part on the radiographic image data and to correct the radiographic image data with the computed scatter field. In some implementations, the computer is further configured to receive an initial material estimate from a user before performing the iterative analysis technique. In certain implementations, the two-dimensional detector and the radiation source are mobile and configured to be used in field environments. In some implementations, the radiation source is a multi-energy radiation source. In certain implementations, the iterative analysis technique is a mixed variable analysis technique, and the computer is further configured to determine an interface location for one or more layers of the object from a solution space of continuous variables.

The example embodiments disclosed herein also include a system, comprising: a detector for detecting radiation from an unknown object and for producing detector data representative of the radiation detected from the unknown object; and a computer configured to input the detector data from the detector and to determine one or more materials that form the unknown object by using an iterative analysis technique that selects the one or more materials from hierarchically arranged solution spaces of discrete material possibilities and that selects layer interfaces from a set of continuous variables. In some implementations, the iterative analysis technique simultaneously performs the selection of the one or more materials with the selection of layer interfaces. In certain implementations, the system further comprises a radiation source configured to interrogate the unknown object, and the iterative analysis technique simultaneously performs the selection of the one or more materials with the selection of layer interfaces using both radiography data generated using the radiation source and the detector data.

The foregoing and other objects, features, and advantages of the disclosed technology will become more apparent from the following detailed description, which proceeds with reference to the accompanying figures.

BRIEF DESCRIPTION OF THE DRAWINGS

FIGS. 9-21 are screenshots from an exemplary implementation of the disclosed technology in which exemplary features and aspects of the disclosed technology are illustrated.

DETAILED DESCRIPTION

I. General Considerations

Figure 1:
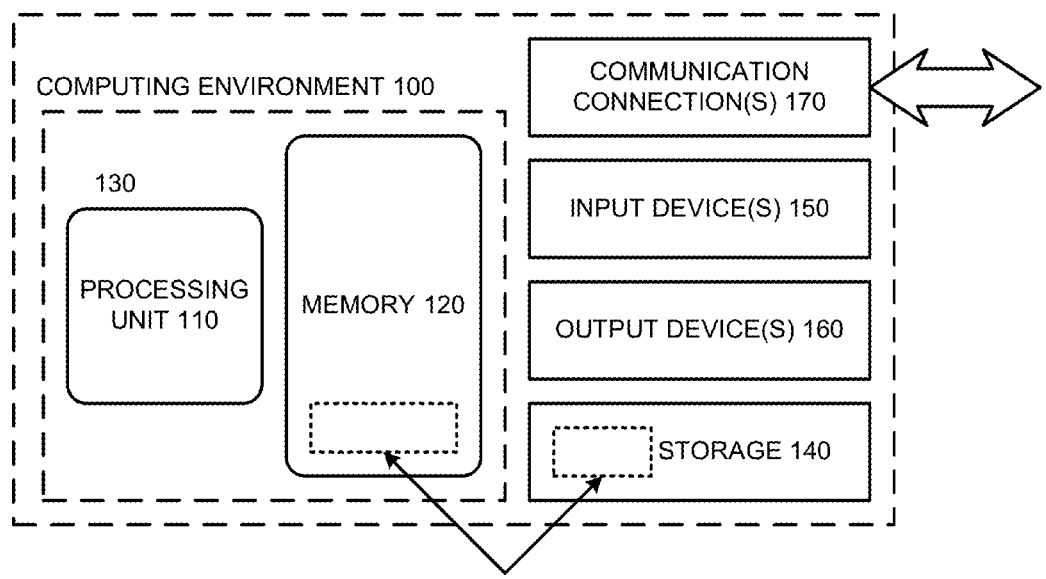
FIG. 1 is a block diagram illustrating a computing environment in which aspects of the disclosed technology can be performed.

Disclosed below are representative embodiments of methods, apparatus, and systems for performing radiography analysis. Certain embodiments of the disclosed technology use mixed variable optimization to perform the analysis. The disclosed methods, apparatus, and systems should not be construed as limiting in any way. Instead, the present disclosure is directed toward all novel and nonobvious features and aspects of the various disclosed embodiments, alone or in various combinations and subcombinations with one another. Furthermore, any features or aspects of the disclosed embodiments can be used in various combinations and subcombinations with one another. For example, one or more method acts from one embodiment can be used with one or more method acts from another embodiment and vice versa. The disclosed methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "determine," "provide," and "optimize," to describe the disclosed methods. These terms are high-level abstractions of the actual operations that are performed. The actual operations that correspond to these terms may vary depending on the particular implementation and are readily discernible by one of ordinary skill in the art. Furthermore, in general, and as used herein, the term "optimal" describes a solution that satisfies some set of criteria better than other solutions according to some parameterization or modeling, which may or may not be optimal in absolute terms depending on circumstances, and the term "optimize" or "optimization" is used to indicate the process of finding such a solution. Additionally, as used herein, the term "and/or" means any one item or combination of any items in the phrase.

II. Exemplary Computing Environments for Implementing Embodiments of the Disclosed Technology Any of the disclosed methods can be implemented as computer-executable instructions stored on one or more computer-readable media (e.g., one or more optical media discs, volatile memory components (such as DRAM or SRAM), or nonvolatile memory components (such as hard drives)) and executed on a computer (e.g., any suitable computer, including desktop computers, servers, smart phones, tablet computers, netbooks, or other devices that include computing hardware). Any of the computer-executable instructions for implementing the disclosed techniques as well as any data created and used during implementation of the disclosed embodiments can be stored on one or more computer-readable media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in Python, C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

The disclosed methods can also be implemented by specialized computing hardware that is configured to perform any of the disclosed methods. For example, the disclosed methods can be implemented (entirely or at least in part) by an integrated circuit (e.g., an application specific integrated circuit ("ASIC") or programmable logic device ("PLD"), such as a field programmable gate array ("FPGA")). The integrated circuit can be embedded in or directly coupled to an electrical device configured to analyze radiographic image data.

FIG. 1 illustrates a generalized example of a suitable computing environment 100 in which several of the described embodiments can be implemented. The computing environment 100 is not intended to suggest any limitation as to the scope of use or functionality of the disclosed technology, as the techniques and tools described herein can be implemented in diverse general-purpose or special-purpose environments that have computing hardware.

With reference to FIG. 1, the computing environment 100 includes at least one processing unit 110 and memory 120. In FIG. 1, this most basic configuration 130 is included within a dashed line. The processing unit 110 executes computer-executable instructions. In a multi-processing system, multiple processing units execute computer-executable instructions to increase processing power. The memory 120 may be volatile memory (e.g., registers, cache, RAM), non-volatile memory (e.g., ROM, EEPROM, flash memory), or some combination of the two. The memory 120 stores software 180 implementing one or more of the described analysis tools or techniques described herein. For example, the memory 120 can store software 180 for implementing any of the disclosed techniques described herein and their accompanying user interfaces.

The computing environment can have additional features. For example, the computing environment 100 includes storage 140, one or more input devices 150, one or more output devices 160, and one or more communication connections 170. An interconnection mechanism (not shown), such as a bus, controller, or network, interconnects the components of the computing environment 100. Typically, operating system software (not shown) provides an operating environment for other software executing in the computing environment 100, and coordinates activities of the components of the computing environment 100.

The storage 140 can be removable or non-removable, and includes magnetic disks, magnetic tapes or cassettes, CD-ROMs, DVDs, or any other tangible non-transitory non-volatile storage medium which can be used to store information and which can be accessed within the computing environment 100. The storage 140 can also store instructions for the software 180 implementing any of the described techniques, systems, or environments.

The input device(s) 150 can be a touch input device such as a keyboard, touchscreen, mouse, pen, trackball, a voice input device, a scanning device, or another device that provides input to the computing environment 100. The output device(s) 160 can be a display device (e.g., a computer monitor, smartphone display, tablet display, netbook display, or touchscreen), printer, speaker, or another device that provides output from the computing environment 100.

The communication connection(s) 170 enable communication over a communication medium to another computing entity. The communication medium conveys information such as computer-executable instructions, compressed or uncompressed image data, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

As noted, the various methods can be described in the general context of computer-readable instructions stored on one or more computer-readable media. Computer-readable media are any available media that can be accessed within or by a computing environment. By way of example, and not limitation, with the computing environment 100, computer-readable media include tangible non-transitory computer-readable media, such as memory 120 and/or storage 140.

The various methods disclosed herein can also be described in the general context of computer-executable instructions, such as those included in program modules, being executed in a computing environment by a processor. Generally, program modules include routines, programs, libraries, objects, classes, components, data structures, and so on, that perform particular tasks or implement particular abstract data types. The functionality of the program modules may be combined or split between program modules as desired in various embodiments. Computer-executable instructions for program modules may be executed within a local or distributed computing environment.

Figure 2:
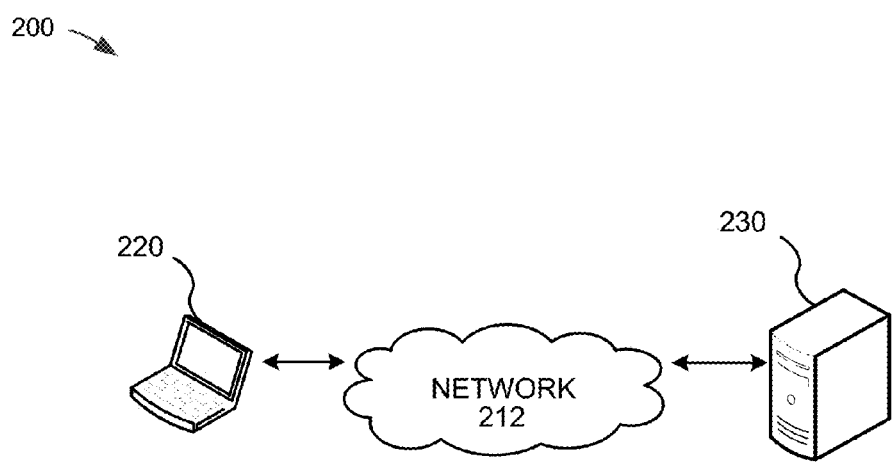
FIG. 2 is a block diagram showing an exemplary network environment in which aspects of the disclosed technology can be performed.

An example of a possible network topology 200 (e.g., a client-server network) for implementing a system according to the disclosed technology is depicted in FIG. 2. Networked computing device 220 can be, for example, a computer running a browser or other software connected to a network 212. The computing device 220 can have a computer architecture as shown in FIG. 1 and discussed above. The computing device 220 is not limited to a traditional personal computers but can comprise other computing hardware configured to connect to and communicate with a network 212 (e.g., smart phones or other mobile computing devices, servers, network devices, dedicated devices, and the like). In the illustrated embodiment, the computing device 220 is configured to communicate with a server 230 (e.g., a remote server) via a network 212. In the illustrated embodiment, the computing device 220 is configured to transmit input data to the server 230 and the server 230 is configured to implement any of the disclosed methods and provide results to the computing device 220. Any of the data received from the computing device 230 can be stored or displayed on the computing device 220 (e.g., displayed as data on a graphical user interface or web page at the computing devices 220). In the illustrated embodiment, the illustrated network 212 can be implemented as a Local Area Network ("LAN") using wired networking (e.g., the Ethernet IEEE standard 802.3 or other appropriate standard) or wireless networking (e.g. one of the IEEE standards 802.11a, 802.11b, 802.11g, or 802.11n or other appropriate standard). Alternatively, at least part of the network 212 can be the Internet or a similar public network and operate using an appropriate protocol (e.g., the HTTP protocol).

III. Introduction to the Disclosed Technology

Described herein are methods, systems, and apparatus that can be used to perform radiography analysis. Embodiments of the disclosed technology can be used in a variety of applications in which the analysis of a radiographic image is desired (e.g., security applications in the field, security applications in a controlled portal (such as a shipping channel, port, airport, train depot, border crossing, and the like), inspection applications, and the like). Furthermore, the disclosed techniques can be adapted for use in a stationary system (e.g., at a controlled portal or laboratory) or in a field-based system (e.g., as part of a system that can be quickly set up and used in the field). For instance, embodiments of the disclosed image analysis techniques can be used for a radiography analysis system used to inspect cargo, vessels, and/or vehicles. The analysis capabilities described herein can also be adapted for passive data analysis.

In general, embodiments of the disclosed technology can reconstruct unknown objects in images in order to identify the size and/or materials in the objects from the image data. In some embodiments, and in contrast to many linear analysis tools, possible materials are identified without additional diagnostic data that supplements the radiograph containing the image. Further, certain embodiments of the disclosed technology can also reconstruct unknown objects from their radiation emissions without the radiographic image data. These embodiments of the disclosed technology can use a combination of radiation emission data and radiographic images to reconstruct unknown objects.

Some exemplary embodiments described herein comprise a diagnostic tool that optimizes a forward model of the 2-D radiographic image in order to determine the size and material composition of an unknown object (e.g., a spherically or cylindrically symmetrical object) by posing the optimization in terms of a mixture of discrete and continuous variables. In particular implementations, the tool reconstructs the unknown object without supplemental diagnostic data. Furthermore, in certain implementations, a fully non-linear forward model is used to reconstruct the unknown object. In some implementations, user expertise or knowledge is incorporated into the analysis to help expedite the solution process. For example, a user may assist the analysis process by helping set initial estimates for interface locations (e.g., radii or other layer boundary or transition locations) observed in the radiograph and/or making an initial estimate of the material(s) in the radiograph. In particular exemplary implementations described herein, the tool is referred to as the "PyRAT" tool ("Python Radiography Analysis Tool"), though this implementation is not limiting. For example, and as noted above, the disclosed technology can be implemented using a variety of different computer languages and have any one or more of the features described herein.

Among the possible benefits that can be realized using embodiments of the disclosed technology is the ability to reconstruct unknown objects having noisy and/or poor 2-D radiographs taken in a field environment without additional radiographs or diagnostic data. For example, embodiments of the disclosed technology can quantitatively evaluate the image data and determine possible object designs that are consistent with the observed data. The mixed variable optimization ("MVO") approach in embodiments of the disclosed technology also allows the user to exclude possible threat materials from the unknown object. This gives the image analyst new quantitative analysis capabilities that do not exist in other tools.

In certain embodiments, the disclosed techniques are used for reconstructing unknown cylindrically or spherically symmetric objects from two-dimensional radiographs taken in a field environment. A nonlinear forward model of the radiograph is generated and used in some embodiments. The problem of identifying the shape and materials in an image can be posed as a MVO problem to find the best thicknesses (expressed as radii in 1-D problems) of layers and set of materials that match the image data. In specific implementations, the solution to this MVO problem is obtained by the class of mesh adaptive direct search ("MADS") algorithms (such as the NOMAD blackbox optimization software or the like). The MADS method is an iterative feasible-point method for estimating the solution of optimization problems where derivatives of objective and constraint functions are not exploited. The MADS method locates an optimal solution over the feasible region by making direct comparison of the objective function values at some trial points lying on a mesh over the domain space. At each iteration, the MADS approach generates a finite number of trial points on the mesh, evaluates an objective function at some (or all) generated trial points with an attempt to find a point with a lower cost function value than the current best iterate point found so far, and then adapts the fineness of the mesh to approach an optimum.

In embodiments of the disclosed technology, reconstructing a 1-D object from a 2-D radiographic image involves the determination of the thickness of the layers in the object and the identification of the materials in each layer. The reconstruction process can be mathematically defined as an inverse problem, which may not have a unique solution. Since the object cannot be mathematically inverted from the data when accounting for all the physical effects, the analysis can instead involve optimizing forward models of the radiography process to determine the object. Some methods to reconstruct the object use templates for the object (educated guesses), approximations in the physics of the forward model, and/or additional diagnostic data to get the inverse solution to converge to an answer. However, these approaches are sensitive to noise in the data and errors in the forward model and/or template. Furthermore, these approaches usually produce non-physical and/or erroneous solutions unless the approximations made represent the actual physics of the problem.

Furthermore, some methods perform a linear inversion (the Abel inversion) on the image. Such methods linearize the physics in the forward model by removing or averaging the energy dependence of the x-ray source, the object's attenuation properties, and the detector response. These methods use regularized parameters that are very hard to define. If incorrect parameters are used, these methods can produce negative densities. Additionally, once the Abel inversion is performed, the inversion data is further processed by correlating real materials to the transmission through the object by using a calibration factor. This calibration information is usually obtained in lab radiographs by taking separate radiographs with known materials to correlate the known material's density to transmission in the image for the source and detector used for the radiograph. These imaging processes that involve calibration information have limited usefulness in field operations, however, as the materials of the unknown object are not known and the libraries of material calibrations usually do not replicate field radiography conditions, causing errors in the inverse calculations.

Embodiments of the disclosed technology represent unknowns in the optimization process as the mixture of discrete or continuous entities. The mixed variable problem formulation helps constrain the possible solutions to a smaller, physically relevant set of solutions. MVO allows for the simultaneous optimization of discrete and continuous variables. This is different from most methods of optimization that only explore the possible solution space using continuous or discrete variables separately.

One approach to solving the MVO problem according to the disclosed technology employs a derivative free, direct search process that allows for discrete and continuous variables. For example, certain embodiments of the disclosed technology use a non-linear non-smooth optimization method where variables are continuous and discrete, and the discrete variables need not have any ordering properties. Such embodiments can employ the class of MADS algorithms implemented in NOMADS. Furthermore, such embodiments allow one to describe the unknown object in the solution space as a discrete and continuous entity, which more accurately represents the physical realities of the object. In embodiments of the disclosed technology, an unknown object is characterized by layers of discrete materials that have interface locations and masses that can range over a continuous spread of values. The discrete properties of different materials in each layer (such as their density and attenuation properties) are implicit in the forward model when the MVO switches the materials in the optimization. Thus, the solution space is constrained to the properties of the possible materials and negative densities are avoided. This speeds up and increases the accuracy of the optimization process. Furthermore, such embodiments allow one to search the discrete space by any group description, or subset of discrete objects, a user selects. Certain embodiments allow the user to utilize any information possible (including their expertise) to constrain the possible materials for each layer so needless optimization is not performed.

IV. Detailed Description of Embodiments of the Disclosed Technology

Figure 3:
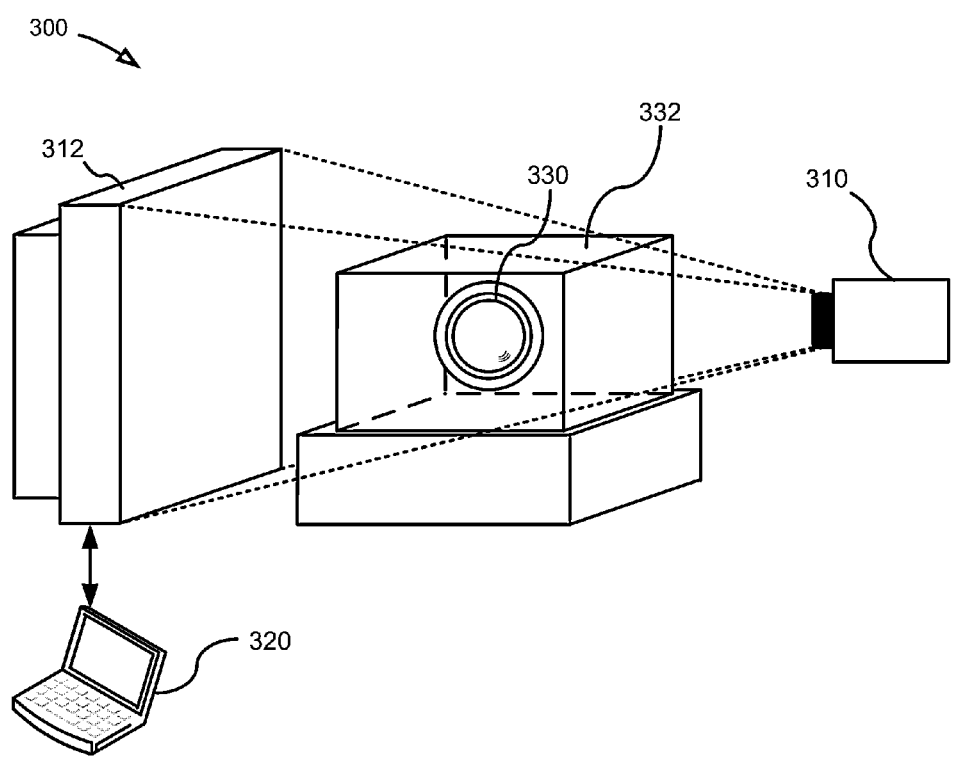
FIG. 3 is a schematic block diagram of an exemplary radiographic system, including a computer for performing analysis of the radiographic image data.

FIG. 3 is a schematic block diagram illustrating an exemplary radiography system 300 according to the disclosed technology. The system 300 is a mobile system that can be used in field applications (e.g., in emergency response situations or at portals where it is desirable to analyze containers or unknown object to determine whether any suspicious or illegal materials may be present). The components of the system 300 are mobile components that are not fixed into a particular location or arrangement and instead can be set up by a user to analyze a particular object in a wide variety of different field environments. This allows the system 300 to be adaptable to a wide variety of environmental conditions. Furthermore, and as more fully explained below, the imaging technique that is used in embodiments of the disclosed technology allows the system 300 to perform image analysis in environments where the imaging conditions are not well controlled. For example, the source to target distances may vary, the target may not be centered on the source and/or detector, the detector may not be perfectly perpendicular to the source and/or target, there may be no collimation of the radiation source, there may be unknown scatter sources, there may be items obstructing the object of interest, and/or there may not be a fiducial marker in the image.

The system 300 in FIG. 3 comprises a radiation source 310 and a detector 312. The radiation source 310 can be any suitable radiation source, such as a discrete-energy or polyenergetic x-ray source (e.g., a Cobalt-60 source or multi-energy Betatron). The radiation source can also be protons accelerated at the target. The detector 312 can be any suitable radiation detector and can have a wide variety of sizes depending on the implementation. For example, the detector can comprise a two-dimensional position-sensitive (or pixelated) detector (e.g., comprising inorganic detectors, such as cesium-iodide-based scintillators). The detector 312 produces data representing the energy detected at each pixel location of the detector for a particular sample period. In the illustrated system 300, the information from detector 312 is conveyed to computer 320, which can be any of the computing environments described above and be programmed to perform any of the disclosed image analysis techniques. For example, the computer 320 may be wirelessly connected or connected through a physical connection to the detector. The block diagram in FIG. 3 further illustrates an object 330 to be analyzed inside of a container 332. In general, the object 330 is a multi-layered cylindrically or spherically symmetric object of interest. Further, in the environment illustrated in FIG. 3, the object 330 is positioned within a container 332 (e.g., a metal container). It is to be understood, of course, that the container 332 may not be present or one or more other obstructions to the object may exist.

In some embodiments of the disclosed technology, the external radiation source is omitted and a detector is used to detect radiation passively from the unknown object. The measured radiation from the unknown object can be used with forward models of the transport of the emitted radiation through the object to reverse engineer (inverse model) the properties of the object. This process is also a mathematical inverse problem analogous to the radiography analysis, where the forward models and constraints are different. Additional details of one non-limiting exemplary approach to solving such an inverse problem are described in Armstrong J. et al., "Identification of Unknown Interface Locations in a Source/Shield System Using the Mesh Adaptive Direct Search Method", 2012 American Nuclear Society Annual Meeting, Report No. LA-UR-12-22365 (Jun. 24-28, 2012).

In general, the image analysis techniques disclosed herein could be described in terms of simplified matrix expressions. In these expressions, the physics of the x-ray projection through the target (object) onto the detector are approximated in terms of linear representations so that the radiography process can be expressed as the matrix equation in Expression (1):

$$\check{P}\vec{x} = \vec{d}_{Lc},  \quad (1)$$

where $\check{P}$ is the source projection matrix, $\vec{x}$ represents the object (or target), and $\vec{d}_{Lc}$ represents the negative natural log of the measured image data. It can be observed from Expression (1) that the unknown target can be determined by:

$$\vec{x} = \check{P}^{-1}\vec{d}_{Lc},  \quad (2)$$

However, radiography physics are non-linear and inverting the projection matrix leads to inaccurate solutions because the radiography physics are massively simplified and the uncertainty in measurements is not considered. Another approach to solving for the unknown object is to minimize the difference (residual) between the modeled image data and the image data actually observed. Thus, $$\vec{d}_c - \vec{d} = \vec{f}(\vec{x}) - \vec{d} = \text{residual} \quad (3)$$

Where $\vec{d}$ is the image data (the image data actually observed by the detector), $\vec{f}(\vec{x})$ is the non-linear representation of the projection, and the "residual" term is the difference between the image data $\vec{d}$ and the calculated image data $\vec{d}_c$ (not the natural log of the calculated data). To address noise and other errors (e.g., errors inherent in the system) that lead to inaccurate and/or non-physical reconstructions, a regularization term $\lambda$ can be added to bias the reconstruction process so that the resulting solution for $\vec{x}$ is not irregular or non-physical. The optimization problem becomes:

$$\min(\|\vec{f}(\vec{x}) - \vec{d}\| + \lambda(\vec{x})) \quad (4)$$

to select $\lambda$ and to then find $\vec{x}$ so that Expression (4) is minimized. The "∥*∥" notation in Expression (4) represents a norm of the difference in mathematical terms. In practice, it is difficult to find $\lambda$ so that the term will correctly account for noise, uncertainty, and the like for all situations and targets, making this approach impractical for field applications.

In embodiments of the disclosed technology, a nonsmooth optimization algorithm for mixed variable problems is used to help identify the object being analyzed. In particular embodiments of the disclosed technology, the technique searches through a solution space of both discrete and continuous variables. For example, in the inversion of the radiograph, the unknown target is treated as a combination of discrete and continuous entities. In certain embodiments, for instance, the materials in a layer of the object being analyzed are treated as discrete variables as part of the image analysis process (as opposed to continuous variables). In particular implementations, the interface locations of the layers in the image are treated as continuous variables, the number of layers is treated as a discrete variable, and the materials and nominal densities of the materials in each layer are treated as discrete variables. In such implementations, the problem to be solved is to find $\vec{x} \in \Omega$ to minimize:

$$\|\vec{f}(\vec{x}) - \vec{d}\| \quad (5)$$

where $\vec{x}$ is the target properties, $\vec{d}$ is the image data, $\vec{f}(\vec{x})$ is the non-linear projection mapping from the source through the target to the detector (also referred to as the forward model), and $\Omega$ is the space of "feasible solutions". The parameters in $\vec{x}$ comprise values that describe the number of layers observed in the object being analyzed, the interface locations of the layers (recall that the object is spherical or cylindrical), and the material in each layer. In particular embodiments, the set of feasible solutions, $\Omega$, comprises constrained values of $\vec{x}$ for which the interface locations of the layers are increasing and the possible materials in each layer are drawn from a set selected by the user.

For passive data analysis, embodiments of the disclosed technology can be adapted to the case where data comprises measured gamma emissions, measured neutron flux, and/or inferred multiplication from measured neutron correlations. For passive data analysis, $\vec{x}$ has the same object properties and feasibility space as those used in the radiography analysis. In these embodiments, the data $\vec{d}$ is the passive data mentioned above. The forward model $\vec{f}(\vec{x})$ represents the radiation emitted in the object, the transport of the radiation through the layers of material surrounding the radiation source, and their measurement in the detectors. Further, in the case of passive data, the detectors may not be two-dimensional image detectors, but can instead be a detector configured to detect gamma emissions and/or neutron flux. For passive data analysis, the optimization process finds the best material layers to match the attenuation and scatter of the emitted radiation through the materials surrounding the radiation source that are measured by the detector. Thus, the resulting optimization problem is analogous to the radiography optimization described herein and makes determining the object from the combination of radiography and passive data a logical extension of the technology disclosed herein. In addition, the optimization process can be modified to vary the source strength, material densities, and other properties of the object when different properties of the object are known.

For data analysis using passive and radiography data simultaneously, embodiments of the disclosed technology can be adapted to the case where data comprises measured gamma emissions, measured neutron flux, inferred multiplication from measured neutron correlations, and radiography data. For this analysis, $\vec{x}$ has the same object properties and feasibility space as those used in the radiography and passive data analysis. In these embodiments, the data $\vec{d}$ has two subcomponents comprised of the passive and radiography data mentioned above. The forward model $\vec{f}(\vec{x})$ likewise has two subcomponents represented by the forward model for the passive data analysis and the forward model for the radiography analysis. In this analysis, the forward models and data sets are defined as multi-objective functions and multi-objective optimization is used to determine the object properties.

Figure 4:
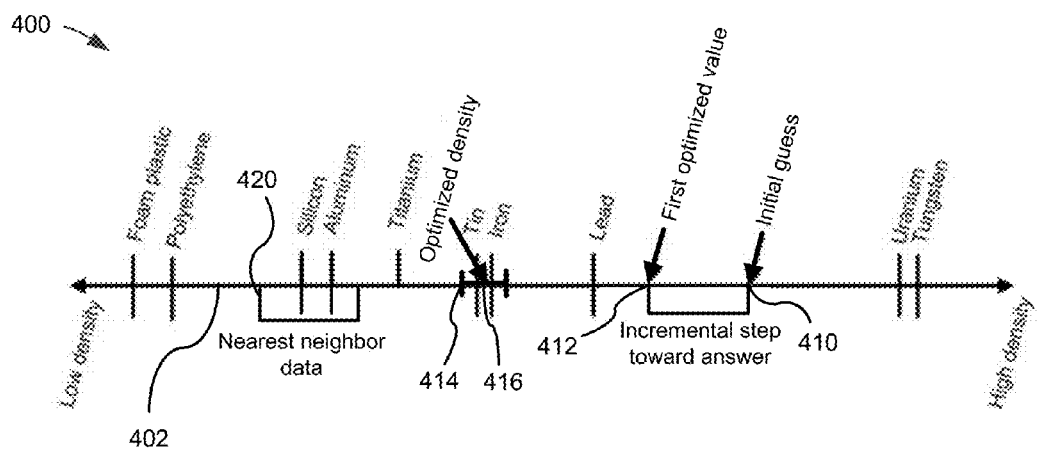
FIG. 4 is a schematic block diagram of an exemplary solution space for a continuous variable.
Figure 5:
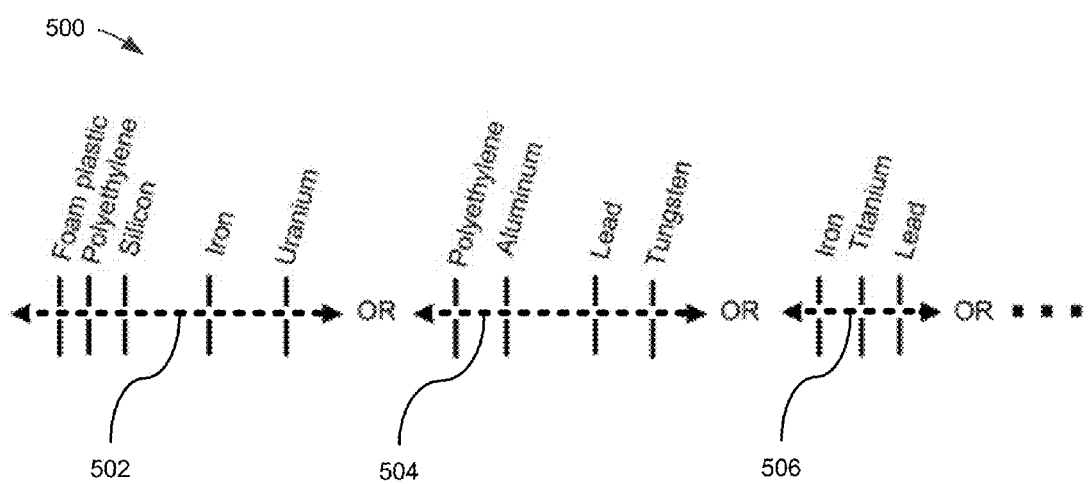
FIG. 5 is a schematic block diagram of three solution spaces for a discrete variable.
Figure 6:
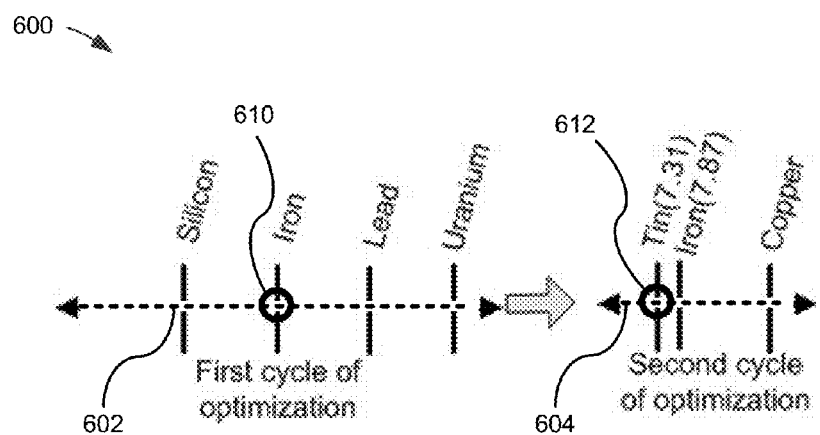
FIG. 6 is a schematic block diagram of two hierarchically arranged solution spaces in which the higher-order solution space has more constrained variable possibilities.

FIGS. 4-6 illustrate the use of "discrete" variables versus "continuous" variables in the context of the disclosed technology. In particular, FIG. 4 is a schematic block diagram 400 illustrating the issues associated with the approach of representing materials in terms of a continuous density value and optimizing the density. In the schematic in FIG. 4, the object has a single layer with a fixed radius. The material densities are optimized in a continuous solution space (as opposed to a discrete solution space) because the densities are non-integer real numbers. In particular, schematic block diagram 400 shows a solution space 402 extending continuously from low density to high density. It is to be understood that because the density variable is continuous, any real number density value along the solution space 402 can be selected as part of the solution process. The optimized density will not often correspond to any actual material as inaccuracies in the forward model and error in the measured data propagate into the selected density during the optimization. Also shown along solution space 402 are identifications of materials having particular densities, but these materials merely correspond to a particular density value and do not illustrate the only available values along the solution space 402. Because the solution space 402 illustrated in FIG. 4 is continuous, any real number density value can be selected. As an example, an initial guess value is illustrated at point 410. As shown, while the illustrated point 410 may represent a reasonable guess for a density value, it does not actually correspond to an actual material. Instead, it merely represents a density value estimated to represent the material. As part of the solution process, an iterative process may occur that alters the density value along the continuous solution space 402. For example, point 412 illustrates a second density value that represents an incremental step toward the solution, which again does not correspond to an actual material.

Range 414 shown in FIG. 4 represents a possible result from an optimization process along the continuous solution space 402 that includes a particular density value (shown as point 416), which is within an uncertainty range 414. As shown, point 416 is located between two possible materials and the uncertainty range 414 encompasses both "tin" and "iron" as possible materials for the particular material being analyzed. The uncertainty represented by range 414 requires the analyst to make a post-optimization decision on which material fits the data based on no radiographic criteria. In particular, an optimization process using only a continuous solution space such as solution space 402 cannot take advantage of the limited material possibilities for the optimal density. The continuous solution space 402 shown in FIG. 4 thus illustrates several drawbacks of determining a material of an object using a continuous solution space.

FIG. 5 is a schematic block diagram 500 illustrating three possible solution spaces 502, 504, 506 that comprise discrete density variables for possible materials where discrete density variables take their values from a finite pre-defined list. In particular, each of the solution spaces 502, 504, 506 includes discrete density values that correspond to real and particular materials. As indicated by the dashed lines along the solution space, the only available density values are those that correspond to real materials. Furthermore, the discrete density values illustrated in FIG. 5 represent an initial solution space that covers a broad range of density values in which the discrete density values available are relatively distinct and spread apart from one another. For example, none of the initial (highest-order) solution spaces 502, 504, 506 includes two materials whose density values are within a certain range from one another (no ordering property). With reference to FIG. 4, for instance, "silicon" and "aluminum" are shown as being within a certain range (e.g., within 0.4 grams per cubic centimeter) by bracket 420. By contrast, the solution spaces 502, 504, 506 are selected to only include materials that are different from one another by more than 0.4 grams per cubic centimeter. It should be understood that any range or difference of density values can be used to differentiate the materials in the solutions spaces of FIG. 5. Furthermore, the solution spaces can be selected so that "nearest neighbor" materials are not found together in the initial (highest-order) solution space (e.g., two materials that are neighbors on the periodic table). In other embodiments, the solution spaces can be determined according to any selection of discrete materials (including materials that are close in density and as nearest neighbors). Indeed, the solution spaces of discrete variables can be determined according to a wide variety of criteria. For example, a user with direct knowledge of the environment in which the object is found can help select possible materials. This allows expert judgment in the selection of possible materials to be directly incorporated into the optimization process.

Figure 7:
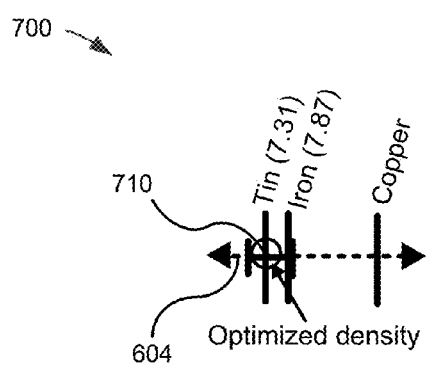
FIG. 7 is a schematic block diagram of a solution space illustrating a material identified by an iterative process involving the use of the hierarchically arranged solution spaces of FIG. 6.

As noted, the solution spaces represented in FIG. 5 represent initial solution spaces for a particular material. In a further iteration of the solution process, a more complete solution space comprising one or more additional discrete materials can be used to aid the material analysis process. For example, FIG. 6 is a schematic block diagram 600 showing a first solution space 602 for a first iteration in which an initial selection 610 (corresponding to iron) is made, and further showing a second solution space 604 for a second iteration in which a second selection 612 (corresponding to tin) is made. As shown in FIG. 6, the second solution space 604 includes materials in the neighborhood of the initial selection, and thus represents a focused solution space with additional material selections. The available solution spaces used to determine an object material can therefore comprise a hierarchical arrangement or set of solution spaces. Higher-level solution spaces in the hierarchy can comprise selected materials across a broader spectrum of densities, whereas lower-order solution spaces in the hierarchy can comprise additional discrete materials across a smaller spectrum of densities. As illustrated by schematic block diagram 700 FIG. 7, a final density 710 can be selected using a hierarchical solution space (such as solution space 604). Furthermore, because the solution spaces are discrete solution spaces, the solution can correspond to a particular material of a particular density value, rather than a particular density value which may or may not correspond to or within the range of a single material. As a result of using discrete variables taking values from a pre-defined set, the analysis procedure can be performed more quickly, more robustly, and in a manner that more realistically models the possible material(s) that form the object. For example, by using discrete variables without ordering properties, the analysis process favors real materials over mathematically possible outcomes that do not reflect real materials (as in the case of using continuous variables).

Figure 8:
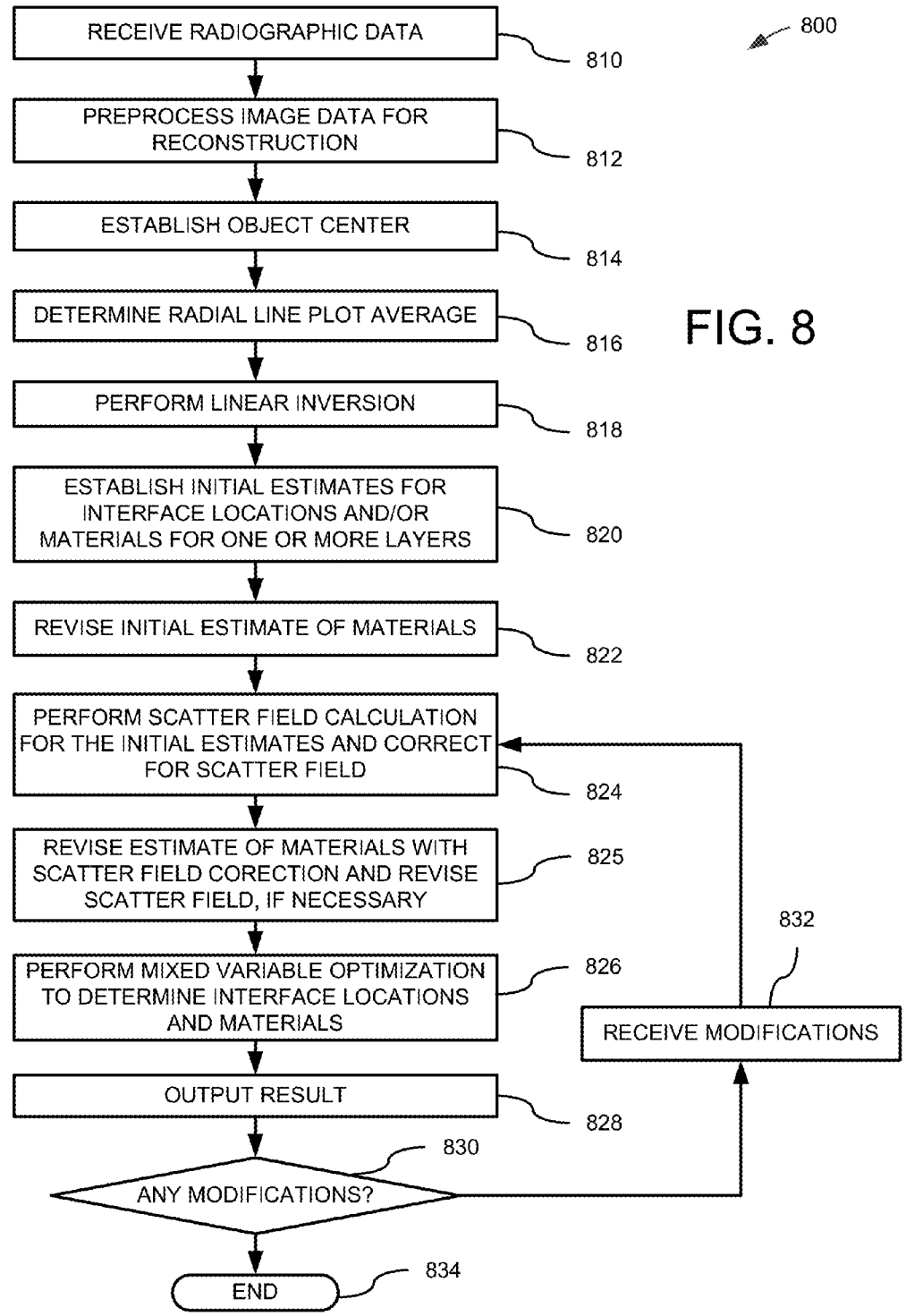
FIG. 8 is a flow chart of a method for performing object analysis according to an exemplary embodiment of the disclosed technology.

FIG. 8 is a flowchart of an exemplary method 800 for performing radiographic analysis according to the disclosed technology (e.g., by using the computer 320 in FIG. 3). The method acts shown in FIG. 8 should not be construed as limiting, as any one or more of the method acts may be omitted, performed in a different order, or supplemented with one or more additional method acts. FIGS. 9-21 are screenshots from an exemplary implementation of the method shown in FIG. 8 that further illustrate aspects of the disclosed method. The particular interfaces, features, and capabilities illustrated by the screenshots in FIGS. 9-21 should not be construed as limiting, as the technology can be implemented using a wide variety of different programs, interfaces, features and capabilities.

Figure 9:
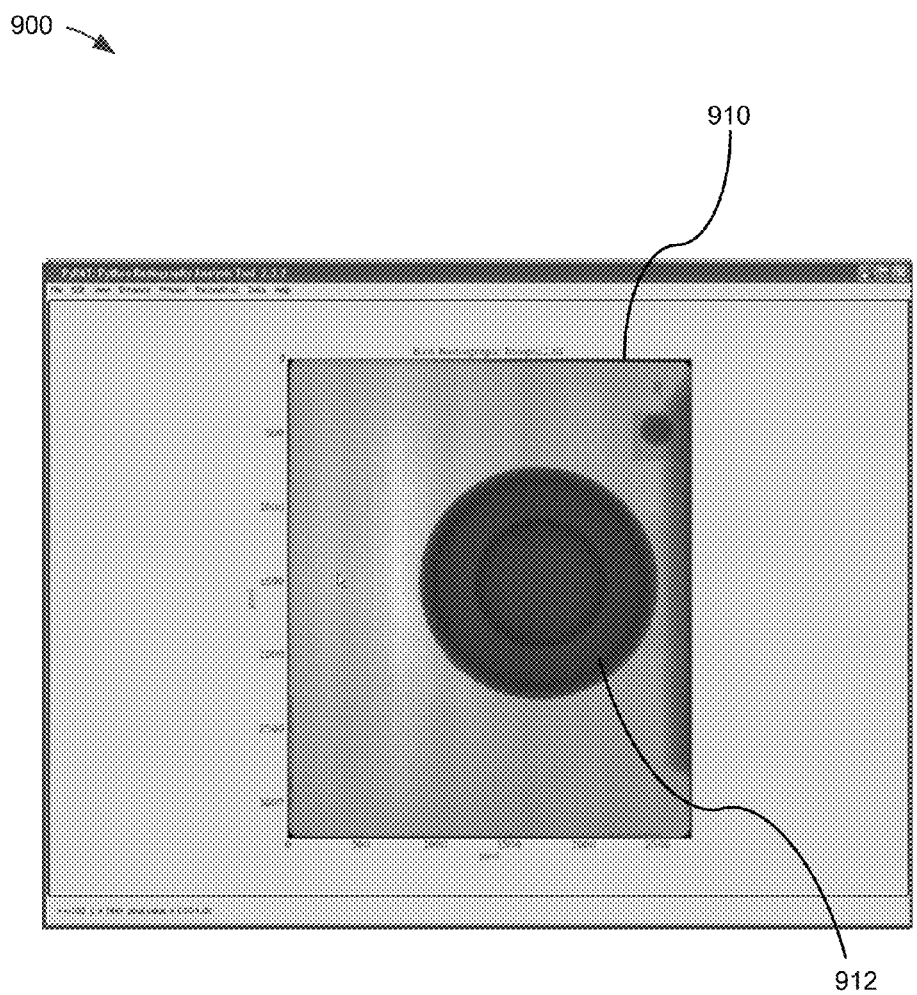

At 810, raw radiographic image data is received (e.g., input from the two-dimensional detector or otherwise loaded or buffered into memory for further processing). Screenshot 900 in FIG. 9 shows an image 910 of the raw radiographic image data. The image 910 is a two-dimensional image comprising pixel values across a range of x-y coordinates of the two-dimensional detector. A multi-layer object 912 that is cylindrically symmetrical can be observed in the image 910. The radiographic image data can be obtained directly from the detector, or can be accessed from a database of image data files (e.g., a database that is populated with data from the detector).

Figure 10:
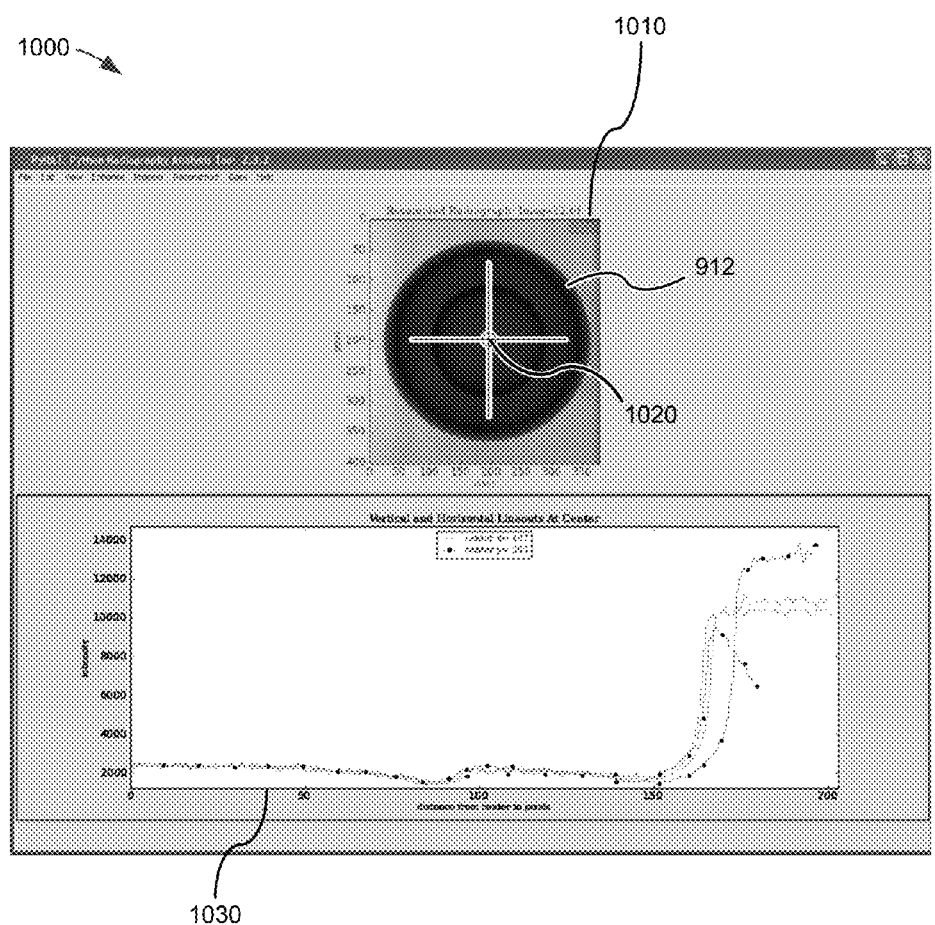
Figure 11:
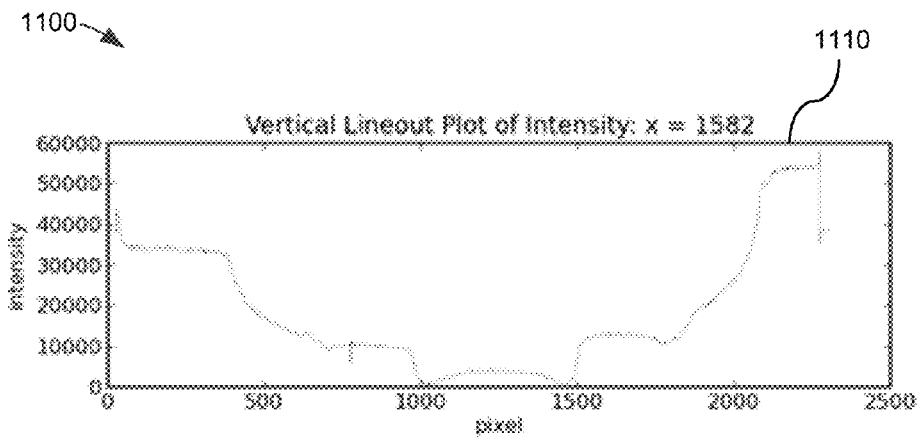
Figure 12:
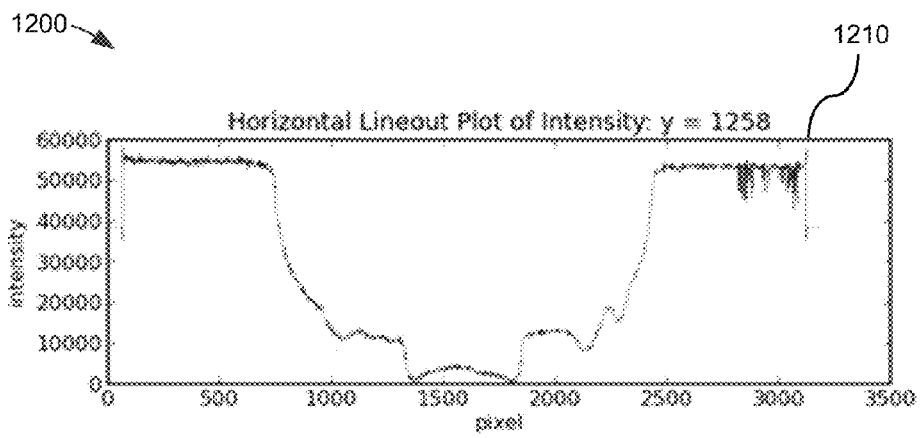

At 812, preprocessing is performed on the image data in order to prepare the image for further analysis. For example, the image can be cropped to better center the object of interest in the image, a smoothing operation can be performed, a resampling operation can be performed that adjusts the pixel size, an image normalizing process can be performed, and/or masking of unwanted features in the image can be performed. Any one or more of the preprocessing procedures can be performed automatically (without further user input) or can rely at least in part on input from a user. For example, in embodiments in which cropping is performed, a user can manually select how cropping should be performed (e.g., using a click and drag operation). Furthermore, in embodiments in which masking is performed, the user can manually identify one or more image portions to mask. Similarly, a user may guide the resampling, smoothing, normalizing process by selecting parameters for performing any of those processes. Screenshot 1000 in FIG. 10 shows a cropped and resampled image 1010 of the image 910 from FIG. 9. As can be seen, the object 912 is relatively centered in the cropped and resampled image 1010. In certain implementations, vertical and horizontal diametrical line plots can also be generated and displayed as part of method act 812. For instance, FIG. 11 shows an image 1110 of an exemplary vertical line plot along a vertical line at x pixel value "1582". FIG. 12 shows an image 1210 of an exemplary horizontal line plot along a horizontal line at y pixel value "1258". As seen, the images 1110, 1210 show the diametrical line plots in terms of pixel intensity values versus vertical or horizontal pixel location.

At 814, the center of the object is established. In certain implementations, the user selects the center of the object (e.g., using a point and click operation or by manually entering the x and y coordinates). The user can be aided by vertical and/or horizontal plot lines (such as the vertical plot line in image 1110 or the horizontal plot line in image 1210) to determine the center. In some embodiments, radial plot lines are computed to aid the user in selecting the center. For example, from the center of the object identified from method act 814, one or more radial plot lines can be determined in which the pixel intensity values are computed along a radial line from the center to the edge of the image. In the image 1010 shown in FIG. 10, for example, four radial directions are used to assess the symmetry of the center point illustrated on the object. The lines are a vertical line from the center to the top of the image, a vertical line from the center to the bottom of the image, a horizontal line from the center to the left of the image, and a horizontal line form the center to the right of the image. FIG. 10 also shows image 1030 in which the radial plot lines for these four directions are displayed. As seen in plot 1030, four plot lines are displayed in terms of pixel intensity value versus distance from center in pixel units. The more the four lines in plot 1030 overlap, the better the center selection.

In other implementations, the center is found automatically using suitable software (e.g., a software function that detects the edges of the cylindrical or spherical object and computes the center based at least in part on the detected edges or that uses one or more of the vertical and/or horizontal plot lines (such as the vertical plot line in image 1110 or the horizontal plot line in image 1210) to determine the center). Screenshot 1000 in FIG. 10 further shows a selected center 1020 of the image 1010. In the illustrated embodiment, the user selected the center 1020 of the object to be analyzed.

Figure 13:
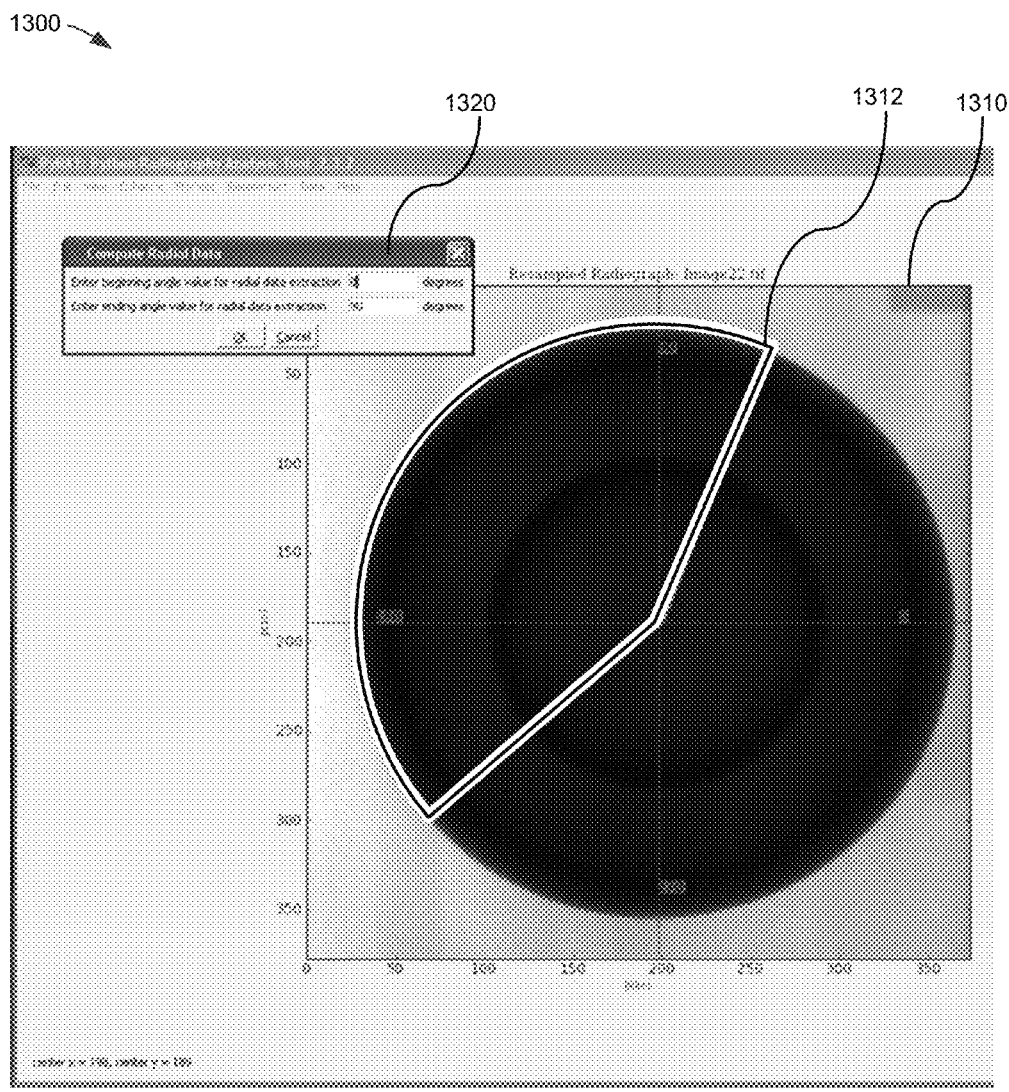

Once the center is selected, and at 816, a radial plot of intensity can be extracted for analysis. This is accomplished, for example, by averaging the data over a "pie slice" identified by the user. The pie slice selection indicates what part of the object image will be used in the analysis. (In cylindrical objects, the "pie slice" will be replaced by a rectangular region centered about the axis of symmetry.) The pie slice selection provides a limited capability to exclude regions of poor quality data. The user can identify the size of the pie slice by manually entering a beginning angle and a finishing angle for the pie slice or by identifying the pie slice using a click and drag operation. FIG. 13 shows a screenshot 1300 in which a pie slice portion 1312 of a cropped and resampled image 1310 of the object can be selected. In the illustrated embodiment, the pie slice portion 1312 is determined from an input box 1320 in which a beginning angle and a final angle can be selected. From the identified pie slice portion, multiple plot lines can be determined and averaged. For example, plot lines along every 1°, 2°, 5° or other radial degree can be determined and averaged. Averaging the data over the angles selected help reduce noise in the radial data. This is evident from the example shown in the radial lineout data shown in plot 1030 of FIG. 10 and from the curves in FIGS. 14 and 15.

Figure 14:
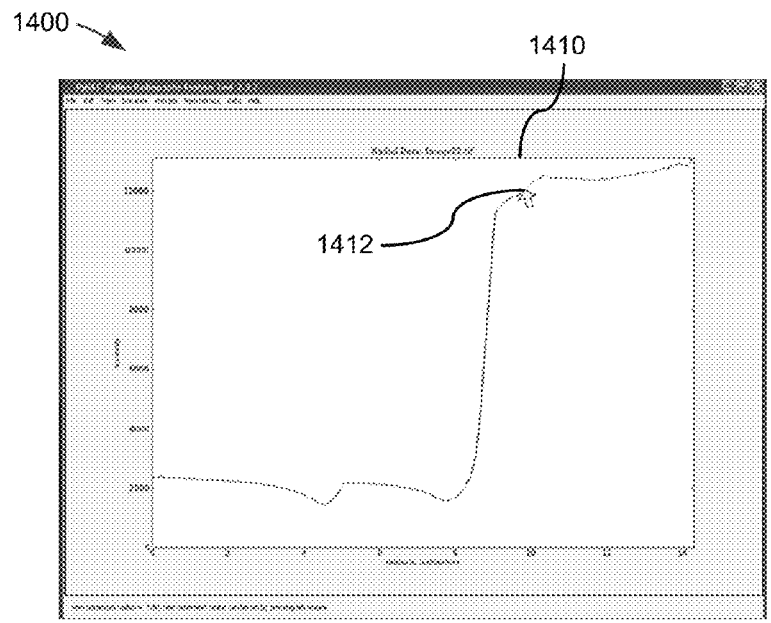
Figure 15:
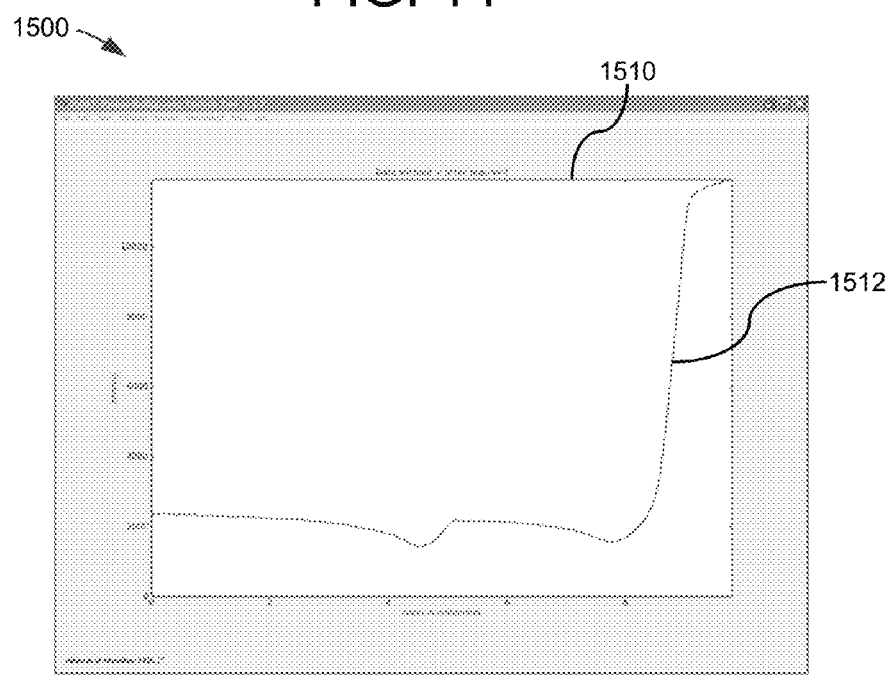

Furthermore, as part of the process of determining the radial line plot average, the average plot line can be trimmed or cropped so as to exclude data that is extraneous to the analysis of the object of interest (e.g., data that is unrelated to the object of interest). In particular embodiments, the user can identify a portion of the average radial plot line to exclude. For instance, screenshot 1400 in FIG. 14 shows an image 1410 of a radial line plot average in which the user is allowed to select a radial point 1412 (also shown by the arrow) where the radial line plot average is to be cropped. Screenshot 1500 in FIG. 15 shows an image 1510 of the resulting cropped radial line plot average 1512. In other embodiments, the radial line plot average is not cropped, or the process is performed automatically using an appropriate software procedure.

Figure 16:
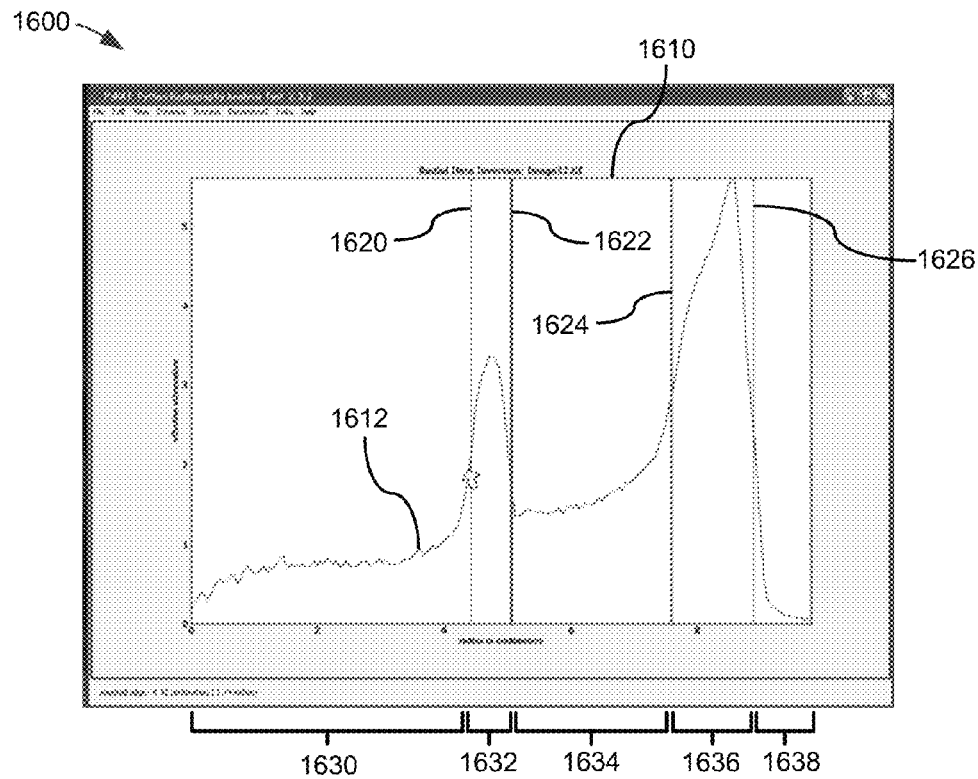
Figure 17:
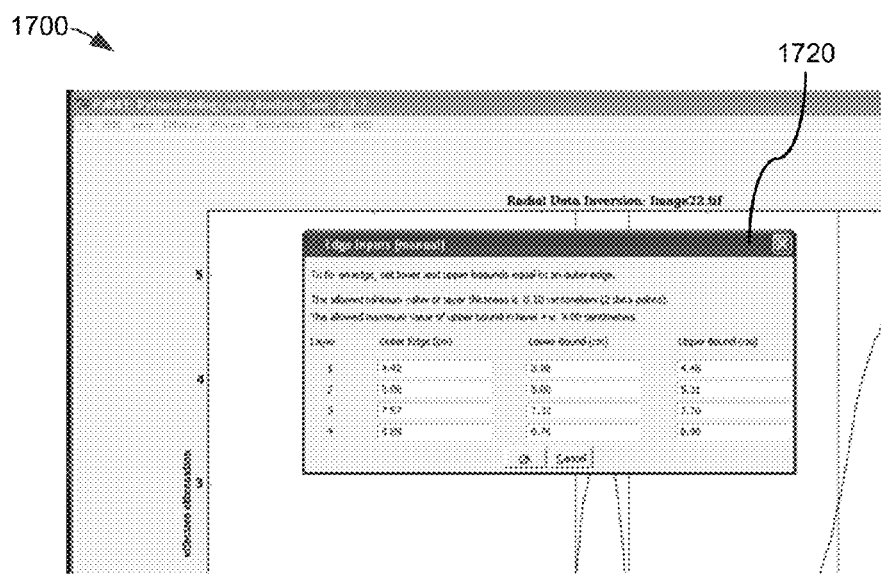
Figure 18:
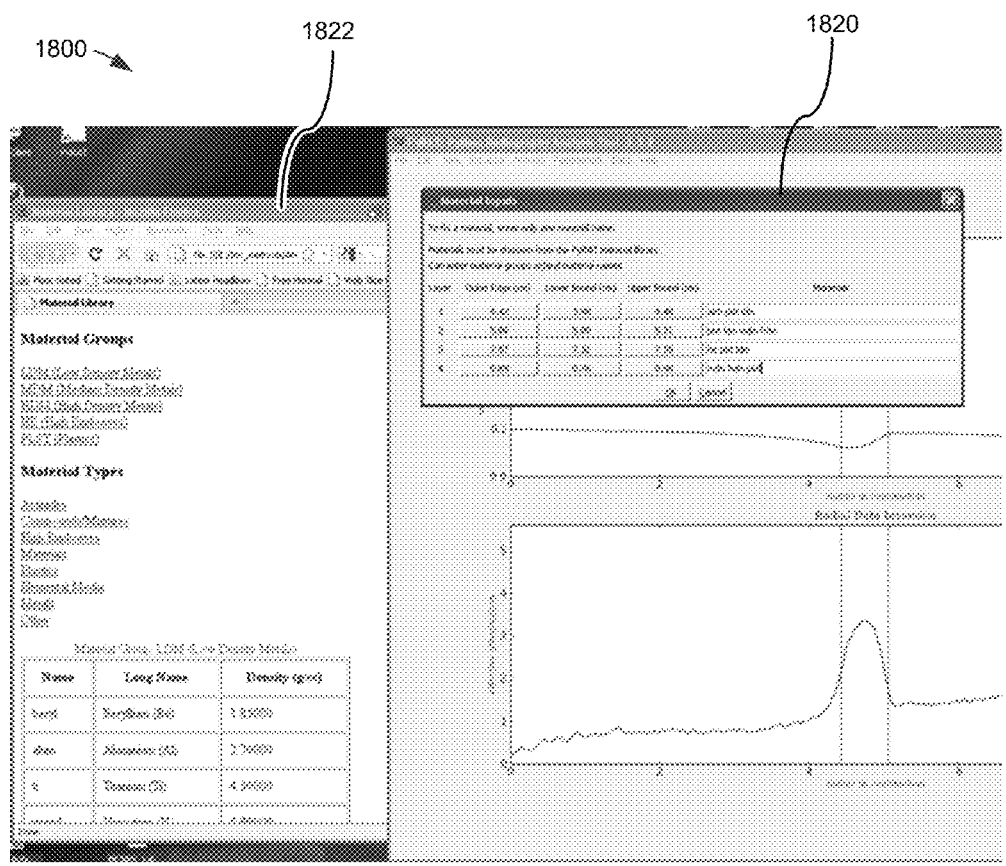
Figure 19:
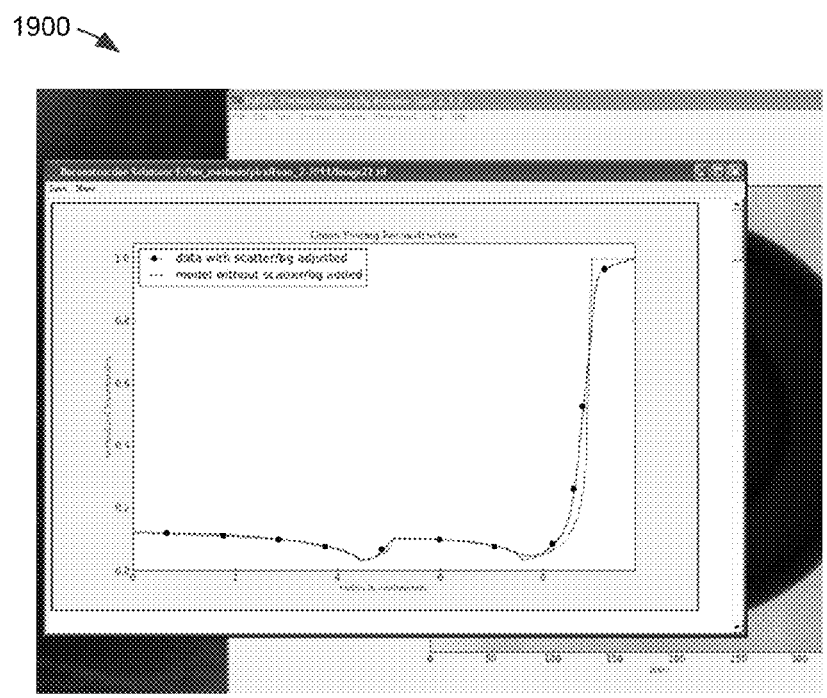

At 818, a linear inversion of the radial line plot average is determined. For example, a linear inversion of the radial line plot average from method act 816 is performed. A variety of linear inversions can be performed, but in certain embodiments, the linear inversion comprises the Abel inversion. The ability to use a linear inversion to help analyze the object is a result of the object's symmetry (e.g., the object's cylindrical or spherical symmetry), which allows the object to be collapsed to a single radial plot (for this reason, the resulting data or object is sometimes referred to as "one-dimensional"). However, because energy dependency is not captured as part of this inversion process, the use of linear inversions in uncontrolled environments (potentially with multi-energy radiation sources) is limited. In the described embodiment, for instance, data from the linear inversion is useful because it can be quickly computed and can help identify the interface locations (e.g., radii) of object layers (and potentially also an initial estimate of materials). The data resulting from the linear inversion can then be displayed to the user as a plot. As a result of the process of averaging the radial line plots and determining the linear inversion, the two-dimensional data is effectively transformed into a single line plot. Screenshot 1600 in FIG. 16 shows an image 1610 of the linearly inverted data 1612. In particular, image 1610 shows the linearly inverted data 1612 as a plot of effective attenuation versus radius. As can be seen from the image 1610, the effective attenuation along the radius of the object of interest includes clearly identifiable differences (e.g., changes in level and/or slope) that indicate differences in material makeup of layers of the object and locations of the layer boundaries in the object. In particular, the inverted data shows the different layers of different materials that form the object of interest.

At 820, initial estimates of the interface locations and/or materials are established. For example, estimates of the layer edges that indicate the radii of such layer can be determined. In image 1610, for instance, a user can select layer transitions 1620, 1622, 1624, 1626 by pointing and clicking the image 1610 at particular radii where attenuation gradients are observed. The different layer edges may be designated by different colors or labels, or other indications. In image 1610, as a result of the layer edge estimates, five layers 1630, 1632, 1634, 1636, 1638 are identified. In certain embodiments, the layers are identified manually and may include constraints for the acceptable radii for the layers. For instance, screenshot 1700 shows a layer selection window 1720 in which a user can manually select the radius for a layer edge for a particular layer (labeled as the "outer edge"), along with a lower and upper bound for a respective layer edge to constrain the solution space during the optimization process performed later. In further embodiments, the initial estimates of the layer transitions are determined automatically by a suitable software procedure (e.g., a software procedure that detects significant changes in the gradient (or slope) of the inverted image data. Additionally, in some embodiments, initial estimates of the material in one or more of the identified layers are input. The inputs can be received, for example, from the user and can be based on some knowledge of the user of the particular object being analyzed. Screenshot 1800 in FIG. 18, for example, includes a material input window 1820 that allows a user to input one or more initial estimates for the material for one or more of the layers determined Also shown in screenshot 1800 is a material library window 1822 that allows the user to obtain and review characteristics of particular materials (e.g., the window 1822 can be a window from a web browser accessing a material database describing various characteristics of possible materials). By allowing a user to input initial estimates, experience and knowledge from a user of the particular environment in which the object analysis object process is being can be leveraged and used to increase the speed and certainty of the analysis process. For instance, the user may be able to observe that an outer layer is clearly "lead", whereas the interior may be unknown but suspected to be a plastic material or other material. The initial estimates may be rough estimates and, as discussed below, may be revised later by the user. In other embodiments, initial estimates are determined automatically and can be based, for instance, on the observed attenuation values and a database of known materials with similar attenuation values. In some embodiments, a linear inversion is not performed (or not used to establish the initial estimates). Instead, the initial estimates are made from a radial line plot. In still other embodiments, no material estimates are input at this stage.

At 822, the selection of initial materials is refined. For example, in particular embodiments, an optimization process is performed that is constrained to just the selection of materials. For example, an optimization procedure can be performed (e.g., using the NOMAD software) but with the material variable being the only variable solved. Furthermore, the material refinement process at 822 may involve using multiple hierarchies of discrete material solution spaces as illustrated in FIG. 6 above. In this process, an adjustment factor can be used to account for scatter and background effects that are not modeled in the forward model used at this stage of the inversion process. The adjustment factor can be applied to the image data so the forward model and the image data can be compared. This process can be repeated until an adjustment factor can be obtained such that image data and forward model agree as best as possible. Example results from this process are shown in screen 1900 of FIG. 19.

At 824, a scatter field computation is performed based on the initial estimate for interface locations (e.g., as defined by the process at 820) and materials (e.g., as defined by the process at 822). The scatter field computation is performed to help compensate for the real-world scattering that occurs during the radiograph process, especially in field environments. In certain embodiments, a Monte Carlo simulation is performed to calculate a scatter contribution. The Monte Carlo simulation may be performed using models of a variety of detectors, radiation sources, and system arrangements that may be used in the field. The appropriate models can be selected by the user (e.g., the distance from the object to detector, the radiation source and energy, and/or the detector type). Other scatter computations may additionally or alternatively be used. The resulting scatter field can then be removed from the observed image data in order to generate scattering compensated data. In certain embodiments, an additional background adjustment value can be applied and modified by the user. For example, the background adjustment value can be an adjustment factor used to compensate for unknown physical effects not modeled in the inversion process.

At 825, in particular embodiments, an additional optimization process constrained to just the selection of materials (like process 822) is performed to allow the user to re-evaluate the possible materials in each layer with a scatter field correction. Like process 822, the optimization procedure can be performed using the NOMAD software, but with the material variable being the only variable solved. In this process, the scatter and background adjustment factor is now a background adjustment factor because the scatter is now accounted for in the comparison of the forward model with the image data. This object reconstruction process can be repeated to re-evaluate the background adjustment factor so a value can be selected that provides the best comparison of the forward model and the image data with scatter contributions removed. Once this process is completed, the scatter field can be recalculated with the newest set of materials in each layer (redo process 824.

At 826, a mixed variable analysis process is performed to determine the interface locations and/or material composition of one or more layers of the object. In particular embodiments, a mixed variable optimization process in which one or more variables are treated as discrete variables without an ordering property and one or more other variables are treated as continuous variables is performed. In certain embodiments, for instance, the radii of the layers in the image are treated as continuous variables and the materials in each layer are treated as discrete variables whose values are chosen from a finite pre-defined set. In particular implementations, the number of layers is treated as a discrete variable, and the materials and therefore the material densities in each layer are treated as discrete variables. By using a mixed variable optimization process, and in certain implementations, the discrete variables and continuous variables can be optimized simultaneously or substantially simultaneously. Any suitable analysis or mixed variable optimization procedure can be used (e.g., a non-linear, non-smooth optimization method using the class of MADS algorithms where variables are continuous and discrete). In one exemplary implementation, for example, the NOMAD software is used. Furthermore, in certain implementations, the material of one or more layers are determined using hierarchically arranged solution spaces in which the higher-level material solution spaces do not include all possible material solutions, but instead comprise a subset of less than all possible materials. During subsequent iterations of the material selection procedure, lower-level solution spaces are used in which additional materials in the neighborhood of the material selected from the first iteration are available and included in the lower-level solution spaces. By constraining the solution space initially, the optimization procedure can proceed with increased efficiency and with a higher probability of successfully converging to a solution. Without the constrained solution spaces and the hierarchical arrangement of solution spaces, the process will produce numerous iterations that fail to converge or quickly converge to a particular solution.

Figures 20, 21:
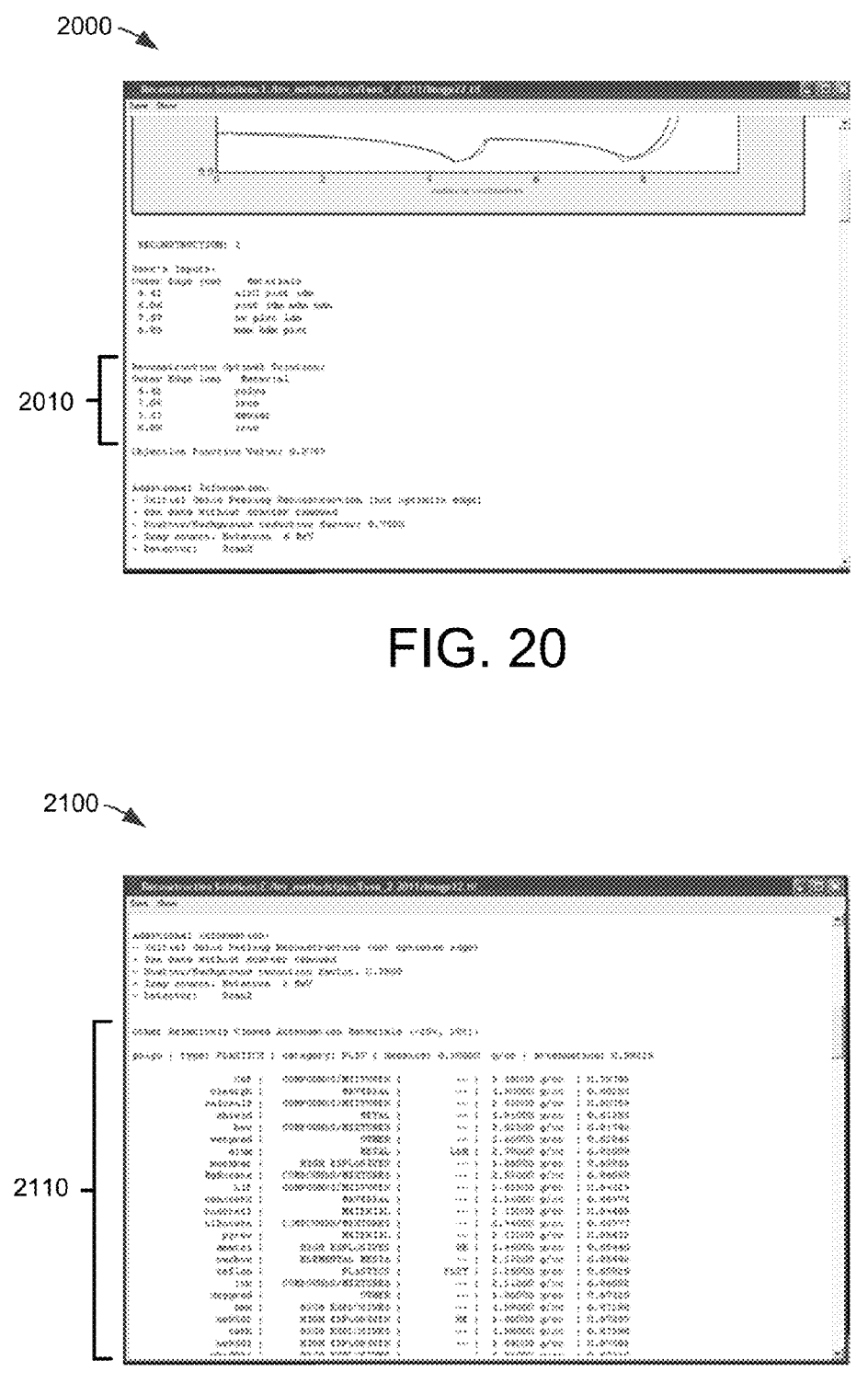

At 828, the interface locations and materials determined at method act 826 are output. For example, the solution determined at method act 826 can be stored on one or more non-transitory computer-readable media, transmitted to another device, and/or displayed on a display device. For instance, the solution can be displayed on a display device as a list of the radii of the object layers along with an identification of the materials determined for each layer. Still further, in some embodiments, additional materials that are similar in density (e.g., within a certain range or percentage of uncertainty) to the identified materials can be displayed along with the materials determined at method act 826. For example, FIG. 20 is a screenshot 2000 showing results 2010 from the mixed variable analysis process at method act 826. As shown, the layers are identified by their outer edge radius and the material determined to form the layer (in the illustrated example: polyurethane, iron, Kevlar, and iron). FIG. 21 is a screenshot 2100 showing results 2110 for other materials that are relatively close to the identified materials in terms of attenuation.

At 830, the inputs for the mixed variable optimization procedure are allowed to be modified. For example, a user can optionally modify one or more of the initial radii determinations and/or material selections. If the inputs are modified, then the revised estimates are received at 832, and the process is repeated from method act 824; otherwise the process ends at 834. In certain embodiments, a representation of the forward model, the residual, and/or the observed image data can be displayed to the user to aid in the selection of modified variables.

Figure 22:
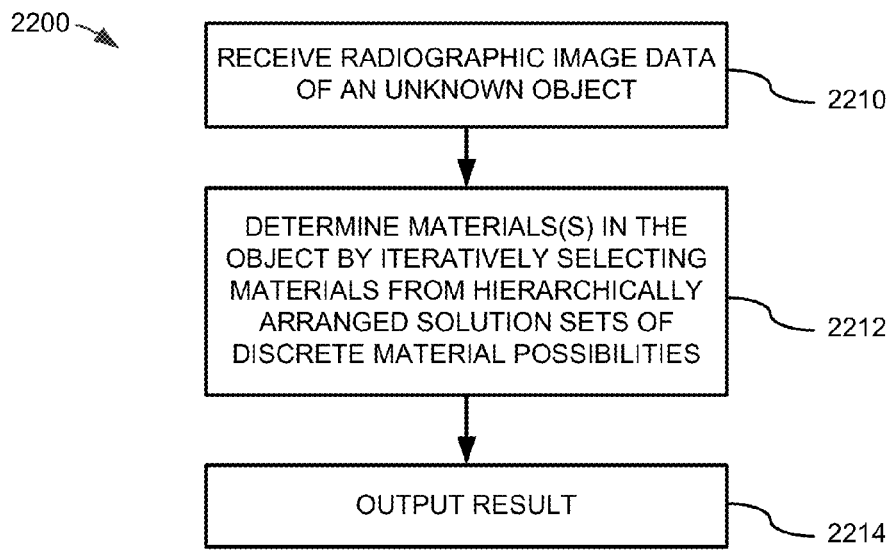
FIG. 22 is a flow chart of another method for performing object analysis according to another exemplary embodiment of the disclosed technology.

FIG. 22 is a flowchart of another more general method 2200 for performing radiographic analysis according to the disclosed technology (e.g., by using the computer 320 in FIG. 3). The method acts shown in FIG. 22 should not be construed as limiting, as any one or more of the method acts may be omitted, performed in a different order, or supplemented with one or more additional method acts.

At 2210, radiographic image data is received (e.g., input from the two-dimensional detector or otherwise loaded or buffered into memory for further processing).

At 2212, one or more materials that form the object are determined by using an iterative analysis technique that selects the one or more materials from hierarchically arranged solution spaces of discrete material possibilities. For example, any of the mixed variable techniques described above can be used. For example, during a first iteration of the iterative analysis technique, a higher-order solution space can be used, while in later iterations, lower-order solution spaces can be used. The lower-order solution spaces can include additional discrete material possibilities that are not available in the higher-order solution space. Further, the additional discrete material possibilities can be closer in density (or other material characteristic) than the possibilities in the higher-order solution space. Any one or more of the additional processing or method acts disclosed herein may also be performed.

At 2214, the one or more materials determined at method act 2212 are output. For example, the solution determined at method act 2212 can be stored on one or more non-transitory computer-readable media, transmitted to another device, and/or displayed on a display device.

Figure 23:
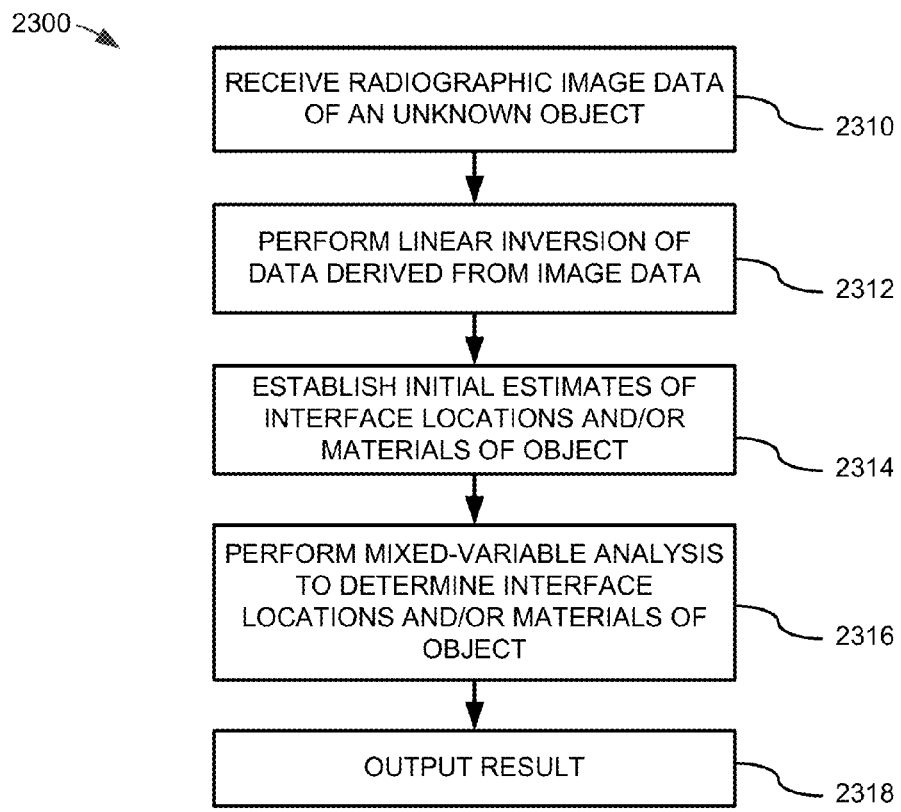
FIG. 23 is a flow chart of a further method for performing object analysis according to a further exemplary embodiment of the disclosed technology.

FIG. 23 is a flowchart of another general method 2300 for performing radiographic analysis according to the disclosed technology (e.g., by using the computer 320 in FIG. 3). The method acts shown in FIG. 23 should not be construed as limiting, as any one or more of the method acts may be omitted, performed in a different order, or supplemented with one or more additional method acts.

At 2310, radiographic image data is received (e.g., input from the two-dimensional detector or otherwise loaded or buffered into memory for further processing).

At 2312, a linear inversion is performed. For example, a linear inversion (such as an Abel inversion) of data derived from the radiographic image can be performed. In particular embodiments, the linear inversion is of one or more radial line plots or an average of radial line plots derived from the radiographic image, such as the radial line plots described above with respect to FIG. 8.

At 2314, initial estimates of interface locations or materials or both interface locations and materials of the object are established. For example, in certain embodiments, the initial estimates can be obtained from a user after the linearly inverted radial line plot is displayed to the user.

At 2316, the interface locations and/or materials are determined using mixed variable optimization in which the interface locations are treated as continuous variables and the materials are treated as discrete variables without ordering property. By using the initial estimates as a starting point, the mixed variable analysis can be made more effective and computationally efficient. In particular embodiments, a mixed variable non-linear non-smooth optimization method is used in which both continuous and discrete variables are considered. For instance, the identification of density of materials and number of layers can be treated as discrete variables, whereas interface locations of layers can be treated as continuous variables. Further, by using a mixed variable optimization process, and in certain implementations, the discrete variables and continuous variables can be optimized simultaneously or substantially simultaneously.

At 2318, the one or more materials determined at method act 2316 are output. For example, the solution determined at method act 2316 can be stored on one or more non-transitory computer-readable media, transmitted to another device, and/or displayed on a display device.

Having illustrated and described the principles of the disclosed technology, it will be apparent to those skilled in the art that the disclosed embodiments can be modified in arrangement and detail without departing from such principles. For example, any one or more aspects of the disclosed technology can be applied in other embodiments. In view of the many possible embodiments to which the principles of the disclosed technologies can be applied, it should be recognized that the illustrated embodiments are only preferred examples of the technology and should not be taken as limiting the scope of the invention. Rather, the scope of the invention is defined by the following claims and their equivalents. We therefore claim as our invention all that comes within the scope and spirit of these claims and their equivalents.

What is claimed is:

1. A radiographic analysis method performed by computing hardware, the method comprising:
receiving radiographic image data of a spherically or cylindrically symmetric object;
performing a linear inversion of data derived from the radiographic image data;
establishing an initial estimate for an interface location of one or more layers of the object;
determining the interface location for the one or more of the layers of the object and identifications of one or more materials forming one or more of the layers of the object, wherein the interface locations are treated as continuous variables and the identifications of the one or more materials are treated as discrete variables during the determining; and
outputting the one or more interface locations and the identifications of the one or more materials forming the one or more of the layers of the object.

2. The method of claim 1, wherein the method further comprises displaying the linear inversion of the radiographic image data, and wherein the establishing the initial estimate comprises receiving input from a user concerning the interface location of one or more layers of the object.

3. The method of claim 1, further comprising establishing a center of the object.

4. The method of claim 3, wherein the method further comprises displaying the radiographic image data, and wherein the establishing the center of the object comprises receiving input from a user concerning the center.

5. A radiographic analysis method performed by computing hardware, the method comprising:
receiving radiographic image data of an unknown spherically or cylindrically symmetric object; and
determining one or more materials forming one or more layers of the spherically or cylindrically symmetric object, wherein the determining is based at least in part on the radiographic image data, and wherein the determining comprises:
during a first iteration, selecting a first material from a first solution space of discrete variables consisting of a first subset of less than all possible materials, and,
during a second iteration, selecting a second material from a second solution space of discrete variables consisting of a second subset of less than all possible materials, the second subset being different from the first subset.

6. The method of claim 5, wherein the second solution space comprises materials that are nearer in density to one another than the materials in the first second solution.

7. The method of claim 5, wherein the second solution space comprises one or two materials that are nearest neighbors to the material selected in the first iteration, and wherein the first solution space is constrained to exclude materials that are nearest neighbors to the material selected.

8. The method of claim 5, wherein the first solution space and the second solution space are part of a hierarchically arranged set of discrete variable solution spaces.

9. The method of claim 5, further comprising selecting an interface location for one or more object layers from a solution space of continuous variables.

10. The method of claim 5, further comprising performing an Abel inversion on a radial line plot derived from the radiographic image data.

11. A system, comprising:
a radiation source;
a two-dimensional detector for detecting radiation originating from the radiation source and being transmitted through an object located between the radiation source and the detector, the two-dimensional detector generating radiographic image data representative of the object; and
a computer configured to input the radiographic image data from the two-dimensional detector and to determine one or more materials that form the object by using an iterative analysis technique that selects the one or more materials from hierarchically arranged solution spaces of discrete material possibilities.

12. The system of claim 11, wherein the iterative analysis technique further selects layer interfaces from a set of continuous variables.

13. The system of claim 11, wherein a first iteration of the iterative analysis technique uses a higher-order solution space than a solution space for a second iteration, the solution space for the second iteration including additional discrete material possibilities not present in the higher-order solution space for the first iteration.

14. The system of claim 13, wherein the additional discrete material possibilities in the second solution space comprise materials that are closer in density to one another than the discrete material possibilities in the first solution space.

15. The system of claim 11, wherein the computer is further configured to compute a scatter field based at least in part on the radiographic image data and to correct the radiographic image data with the computed scatter field.

16. The system of claim 11, wherein the two-dimensional detector and the radiation source are mobile and configured to be used in field environments.

17. The system of claim 11, wherein the object is a spherically or cylindrically symmetrical object.

18. A system, comprising:
a detector for detecting radiation from an unknown object and for producing detector data representative of the radiation detected from the unknown object; and
a computer configured to input the detector data from the detector and to determine one or more materials that form the unknown object by using an iterative analysis technique that selects the one or more materials from hierarchically arranged solution spaces of discrete material possibilities and that selects layer interfaces from a set of continuous variables.

19. The system of claim 18, wherein the iterative analysis technique simultaneously performs the selection of the one or more materials with the selection of layer interfaces.

20. The system of claim 18, wherein the system further comprises a radiation source configured to interrogate the unknown object, and wherein the iterative analysis technique simultaneously performs the selection of the one or more materials with the selection of layer interfaces using both radiography data generated using the radiation source and the detector data.

21. One or more non-transitory computer-readable media storing computer-executable instructions which when executed by a computer cause the computer to perform a radiographic analysis method, the method comprising:
receiving radiographic image data of a spherically or cylindrically symmetric object;
performing a linear inversion of data derived from the radiographic image data;
establishing an initial estimate for an interface location of one or more layers of the object;

determining the interface location for the one or more of the layers of the object and identifications of one or more materials forming one or more of the layers of the object, wherein the interface locations are treated as continuous variables and the identifications of the one or more materials are treated as discrete variables during the determining; and outputting the one or more interface locations and the identifications of the one or more materials forming the one or more of the layers of the object.

22. The one or more non-transitory computer-readable media of claim 21, wherein the method further comprises displaying the linear inversion of the radiographic image data, and wherein the establishing the initial estimate comprises receiving input from a user concerning the interface location of one or more layers of the object.

23. The one or more non-transitory computer-readable media of claim 21, wherein the method further comprises establishing a center of the object.

24. The one or more non-transitory computer-readable media of claim 23, wherein the method further comprises displaying the radiographic image data, and wherein the establishing the center of the object comprises receiving input from a user concerning the center.

25. One or more non-transitory computer-readable media storing computer-executable instructions which when executed by a computer cause the computer to perform a radiographic analysis method, the method comprising:

receiving radiographic image data of an unknown spherically or cylindrically symmetric object; and determining one or more materials forming one or more layers of the spherically or cylindrically symmetric object, wherein the determining is based at least in part on the radiographic image data, and wherein the determining comprises:

during a first iteration, selecting a first material from a first solution space of discrete variables consisting of a first subset of less than all possible materials, and, during a second iteration, selecting a second material from a second solution space of discrete variables consisting of a second subset of less than all possible materials, the second subset being different from the first subset.

26. The one or more non-transitory computer-readable media of claim 25, wherein the second solution space comprises materials that are nearer in density to one another than the materials in the first second solution.

27. The one or more non-transitory computer-readable media of claim 25, wherein the second solution space comprises one or two materials that are nearest neighbors to the material selected in the first iteration, and wherein the first solution space is constrained to exclude materials that are nearest neighbors to the material selected.

28. The one or more non-transitory computer-readable media of claim 27, wherein the first solution space and the second solution space are part of a hierarchically arranged set of discrete variable solution spaces.

29. The one or more non-transitory computer-readable media of claim 27, wherein the method further comprises selecting an interface location for one or more object layers from a solution space of continuous variables.

30. The one or more non-transitory computer-readable media of claim 27, wherein the method further comprises performing an Abel inversion on a radial line plot derived from the radiographic image data.

* * * * *